(12) United States Patent
Schwartz

(10) Patent No.: US 7,918,854 B2
(45) Date of Patent: Apr. 5, 2011

(54) NON-DESTRUCTIVE TISSUE REPAIR AND REGENERATION

(75) Inventor: Herbert E. Schwartz, Fort Wayne, IN (US)

(73) Assignee: Howmedica Osteonics Corp., Mahwah, NJ (US)

( * ) Notice: Subject to any disclaimer, the term of this patent is extended or adjusted under 35 U.S.C. 154(b) by 938 days.

(21) Appl. No.: 11/735,144

(22) Filed: Apr. 13, 2007

(65) Prior Publication Data

US 2007/0185568 A1   Aug. 9, 2007

Related U.S. Application Data

(63) Continuation-in-part of application No. 10/558,926, filed as application No. PCT/US2005/013973 on Apr. 25, 2005.

(60) Provisional application No. 60/565,428, filed on Apr. 26, 2004.

(51) Int. Cl.
*A61B 17/56* (2006.01)

(52) U.S. Cl. .......................... 606/65; 128/898

(58) Field of Classification Search .................. 606/65, 606/69, 72, 73, 77, 86, 213, 218, 232, 216, 606/191–198; 623/1.11, 1.15; 128/898
See application file for complete search history.

(56) References Cited

U.S. PATENT DOCUMENTS

| | | |
|---|---|---|
| 4,484,570 A | 11/1984 | Sutter et al. |
| 4,884,572 A | 12/1989 | Bays et al. |
| 4,968,317 A | 11/1990 | Tormala et al. |
| 4,976,715 A | 12/1990 | Bays et al. |
| 5,041,129 A | 8/1991 | Hayhurst et al. |
| 5,059,206 A | 10/1991 | Winters |
| 5,129,906 A | 7/1992 | Ross et al. |
| 5,152,791 A | 10/1992 | Hakamatsuka et al. |
| 5,236,431 A | 8/1993 | Gogolewski et al. |
| 5,261,914 A | 11/1993 | Warren |
| 5,269,809 A | 12/1993 | Hayhurst et al. |
| 5,370,662 A | 12/1994 | Stone et al. |
| 5,374,268 A | 12/1994 | Sander |
| 5,470,337 A | 11/1995 | Moss |
| 5,500,000 A | 3/1996 | Feagin et al. |
| 5,503,634 A | 4/1996 | Christy |
| 5,522,843 A | 6/1996 | Zang |
| 5,569,252 A | 10/1996 | Justin et al. |
| 5,669,909 A * | 9/1997 | Zdeblick et al. .............. 606/247 |
| 5,681,353 A | 10/1997 | Li et al. |
| 5,683,366 A | 11/1997 | Eggers et al. |

(Continued)

FOREIGN PATENT DOCUMENTS

CA      1292596      12/1991

(Continued)

OTHER PUBLICATIONS

Adams et al., J. of Knee Surgery, Tissue Engineering for Meniscus Repair, vol. 18(1), 2005, pp. 25-30.

(Continued)

*Primary Examiner* — Kevin T Truong
(74) *Attorney, Agent, or Firm* — Lerner, David, Littenberg, Krumholz & Mentlik, LLP

(57) ABSTRACT

A surgical stent made of biocompatible material for implantation in human tissue to enable blood and nutrients to flow from an area of vascular tissue to an area of tissue with little or no vasculature.

59 Claims, 11 Drawing Sheets

U.S. PATENT DOCUMENTS

| | | | |
|---|---|---|---|
| 5,702,462 A | 12/1997 | Oberlander | |
| 5,725,549 A | 3/1998 | Lam | |
| 5,730,744 A | 3/1998 | Justin et al. | |
| 5,824,011 A | 10/1998 | Stone et al. | |
| 5,842,477 A | 12/1998 | Naughton et al. | |
| 5,873,855 A | 2/1999 | Eggers et al. | |
| 5,935,119 A * | 8/1999 | Guy et al. | 604/500 |
| 5,954,747 A | 9/1999 | Clark | |
| 5,976,127 A | 11/1999 | Lax | |
| 5,980,559 A | 11/1999 | Bonutti | |
| 6,056,778 A | 5/2000 | Grafton et al. | |
| 6,068,648 A | 5/2000 | Cole et al. | |
| 6,096,060 A | 8/2000 | Fitts et al. | |
| 6,102,046 A | 8/2000 | Weinstein et al. | |
| 6,146,387 A | 11/2000 | Trott et al. | |
| 6,203,556 B1 | 3/2001 | Evans et al. | |
| 6,306,156 B1 | 10/2001 | Clark | |
| 6,306,159 B1 | 10/2001 | Schwartz et al. | |
| 6,319,270 B1 | 11/2001 | Grafton et al. | |
| 6,338,739 B1 | 1/2002 | Datta et al. | |
| 6,387,111 B1 | 5/2002 | Barber | |
| 6,468,277 B1 * | 10/2002 | Justin et al. | 606/65 |
| 6,503,251 B1 | 1/2003 | Shadduck | |
| 6,511,958 B1 | 1/2003 | Atkinson et al. | |
| 6,514,514 B1 | 2/2003 | Atkinson et al. | |
| 6,517,542 B1 * | 2/2003 | Papay et al. | 606/232 |
| 6,548,569 B1 | 4/2003 | Williams et al. | |
| 6,569,191 B1 | 5/2003 | Hogan | |
| 6,595,990 B1 | 7/2003 | Weinstein et al. | |
| 6,638,237 B1 | 10/2003 | Guiles et al. | |
| 6,660,008 B1 | 12/2003 | Foerster et al. | |
| 6,685,695 B2 | 2/2004 | Ferree | |
| 6,685,728 B2 | 2/2004 | Sinnott et al. | |
| 6,692,499 B2 | 2/2004 | Tormala et al. | |
| 6,695,499 B2 | 2/2004 | Tormalaet et al. | |
| 6,763,836 B2 | 7/2004 | Tasto et al. | |
| 6,780,164 B2 | 8/2004 | Bergheim et al. | |
| 6,838,493 B2 | 1/2005 | Williams et al. | |
| 6,867,247 B2 | 3/2005 | Williams et al. | |
| 6,884,428 B2 | 4/2005 | Binette et al. | |
| 6,932,834 B2 | 8/2005 | Lizardi et al. | |
| 6,972,027 B2 | 12/2005 | Fallin et al. | |
| 7,153,312 B1 | 12/2006 | Torrie et al. | |
| 7,163,563 B2 | 1/2007 | Schwartz et al. | |
| 7,608,098 B1 | 10/2009 | Stone et al. | |
| 2002/0068930 A1 | 6/2002 | Tasto et al. | |
| 2002/0169477 A1 | 11/2002 | Demopulos et al. | |
| 2003/0078600 A1 | 4/2003 | O'Quinn et al. | |
| 2003/0097148 A1 | 5/2003 | Valimaa et al. | |
| 2003/0100859 A1 | 5/2003 | Henderson et al. | |
| 2004/0064081 A1 | 4/2004 | Stanish | |
| 2004/0093032 A1 | 5/2004 | Sinnott et al. | |
| 2004/0230195 A1 | 11/2004 | Kaikkonen et al. | |
| 2004/0260343 A1 | 12/2004 | Leclair | |
| 2005/0033363 A1 | 2/2005 | Bojarski et al. | |
| 2005/0234549 A1 | 10/2005 | Kladakis et al. | |
| 2005/0246023 A1 | 11/2005 | Yeung | |
| 2005/0271704 A1 | 12/2005 | Tu et al. | |
| 2006/0089646 A1 | 4/2006 | Bonutti | |
| 2006/0100627 A1 | 5/2006 | Stone et al. | |
| 2006/0189993 A1 | 8/2006 | Stone | |
| 2006/0190042 A1 | 8/2006 | Stone et al. | |
| 2006/0247600 A1 | 11/2006 | Yeung et al. | |
| 2006/0247642 A1 | 11/2006 | Stone et al. | |
| 2006/0280768 A1 | 12/2006 | Hwang et al. | |
| 2006/0282085 A1 | 12/2006 | Stone et al. | |
| 2007/0067025 A1 | 3/2007 | Schwartz | |
| 2007/0185532 A1 | 8/2007 | Stone et al. | |
| 2008/0027446 A1 | 1/2008 | Stone et al. | |
| 2008/0033487 A1 | 2/2008 | Schwartz et al. | |
| 2008/0065114 A1 | 3/2008 | Stone et al. | |
| 2008/0082128 A1 | 4/2008 | Stone | |
| 2008/0132932 A1 | 6/2008 | Hoeppner et al. | |
| 2008/0140092 A1 | 6/2008 | Stone et al. | |
| 2008/0140093 A1 | 6/2008 | Stone et al. | |
| 2008/0255613 A1 | 10/2008 | Kaiser et al. | |
| 2008/0312689 A1 | 12/2008 | Denham et al. | |
| 2009/0018561 A1 | 1/2009 | Schwartz et al. | |

FOREIGN PATENT DOCUMENTS

| | | |
|---|---|---|
| CA | 2155422 | 8/1994 |
| CA | 2168835 | 8/1996 |
| JP | 03-178652 | 8/1991 |
| JP | 2004-000540 | 1/2004 |
| WO | 93/15694 | 8/1993 |
| WO | 97/32551 | 9/1997 |
| WO | 9921510 | 5/1999 |
| WO | 00/36997 | 6/2000 |
| WO | 03/007784 | 1/2003 |
| WO | 03063713 A1 | 8/2003 |
| WO | 2005104992 | 11/2005 |

OTHER PUBLICATIONS

Amoczky et al., J. of Bone and Joint Surgery, Meniscal Repair Using an Exogenous Fibrin Clot, vol. 70A(8), 1988, pp. 1200-1217.

Fox et al, J. of Arthroscopic and Related Surgery, Treytination of Incomplegte Meniscal Tears,9(4), 1993, pp. 451-455.

Okuda et al., J of Arthroscopic and Related Surgery, Meniscal Rasping for Repair of Meniscal Tear in the Avascular Zone, vol. 15(3),1999, pp. 281-286.

O'Meara, p., Orthopaedic Review, The Basic Science of Meniscus Repair, Jun. 1993, pp. 681-686.

Sgaglione et al., J. of Arthroscopic and Related Surgery, Current Concepts in Meniscus Surgery Resection to Replacement, vol. 19(10), 2003, pp. 161-188.

Zhang et al., Am. J. of Sports Medidne, Repairs by Trephination and Suturing of Longitudinal Injuries in the AvascularArea of the Meniscus in Goats, vol. 23(1), 1995, pp. 35-41.

Smith & Nephew Technique Plus Illustrated Guide—Meniscal Repair with FasT-Fix Suture System.

U.S. Appl. No. 10/983,236.

U.S. Appl. No. 10/984,624.

Supplementary European Search Report issued on Jul. 28, 2008 in connection with corresponding European Application No. EP 05 73 9944.

* cited by examiner

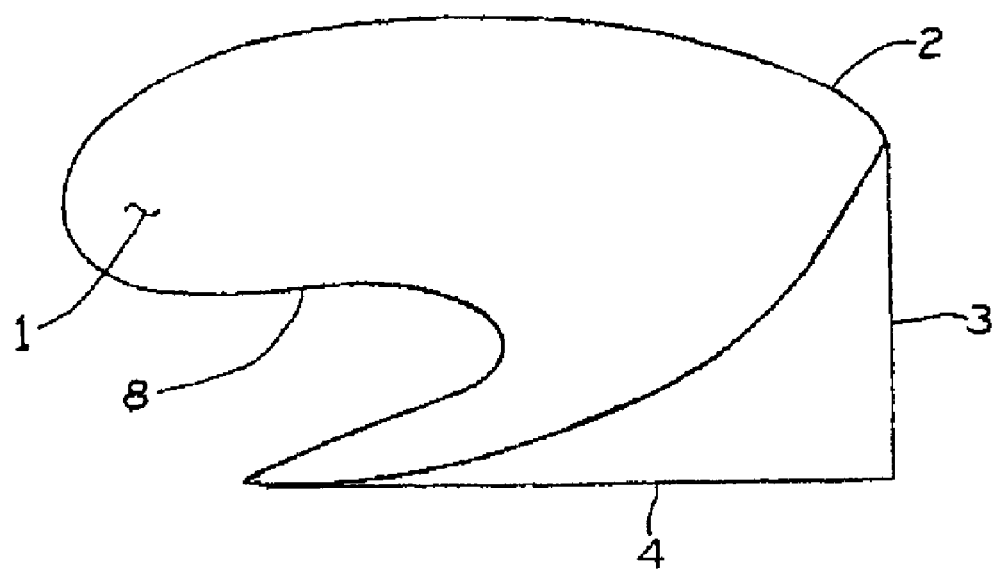
FIG_1
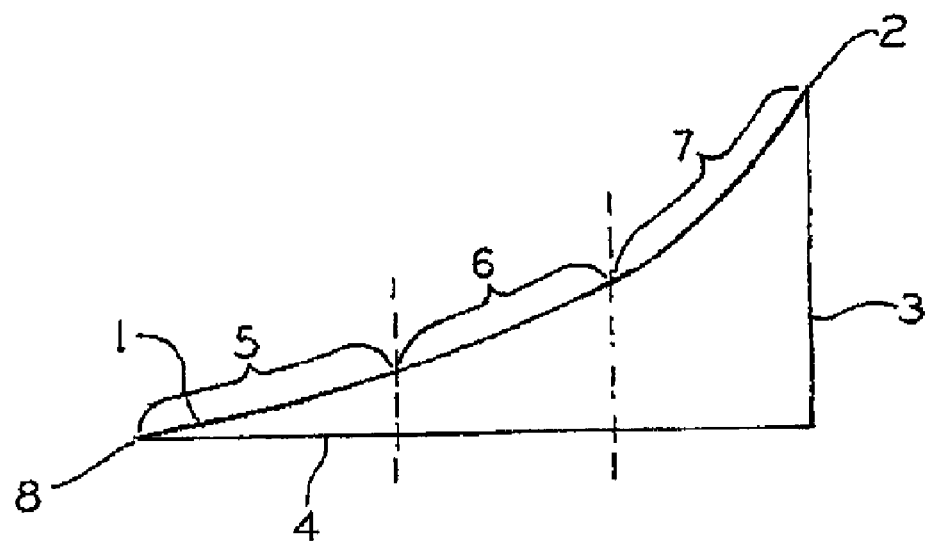
FIG_2

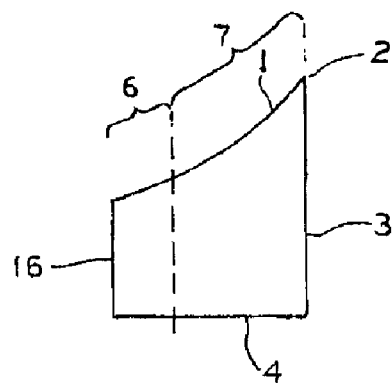
FIG_9
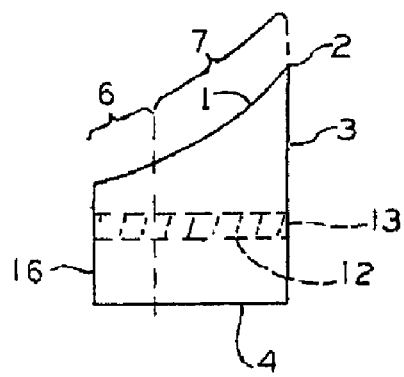
FIG_10
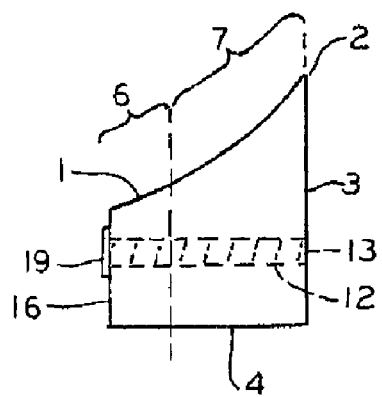
FIG_11
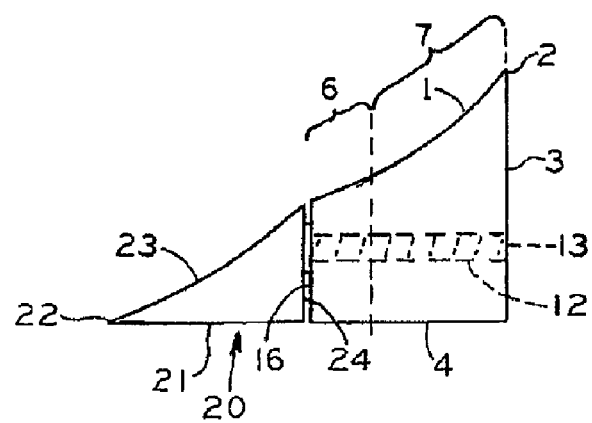
FIG_12

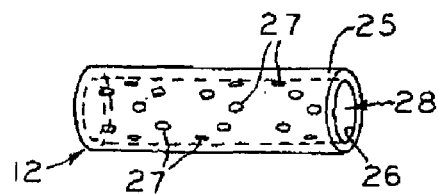
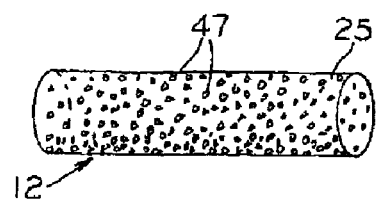
FIG.\_13A      FIG.\_13B
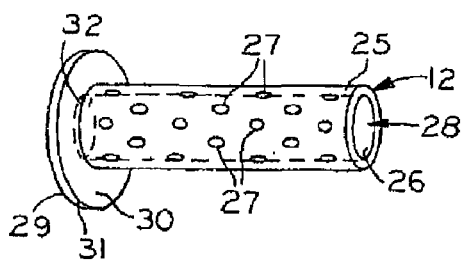
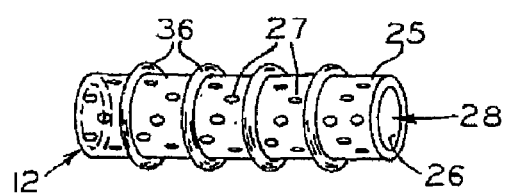
FIG.\_14      FIG.\_15
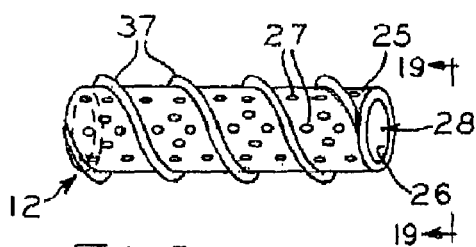
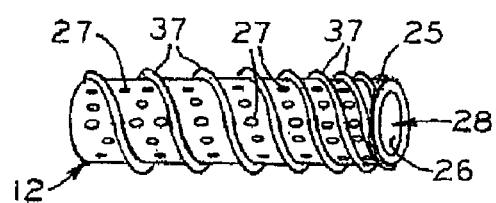
FIG.\_16A      FIG.\_16B
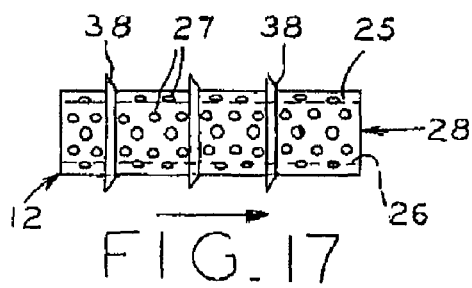
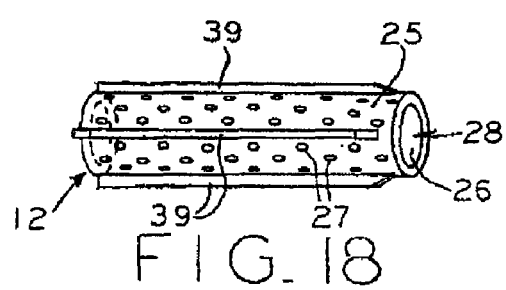
FIG.\_17      FIG.\_18
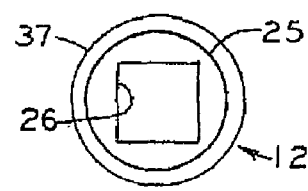
FIG.\_19

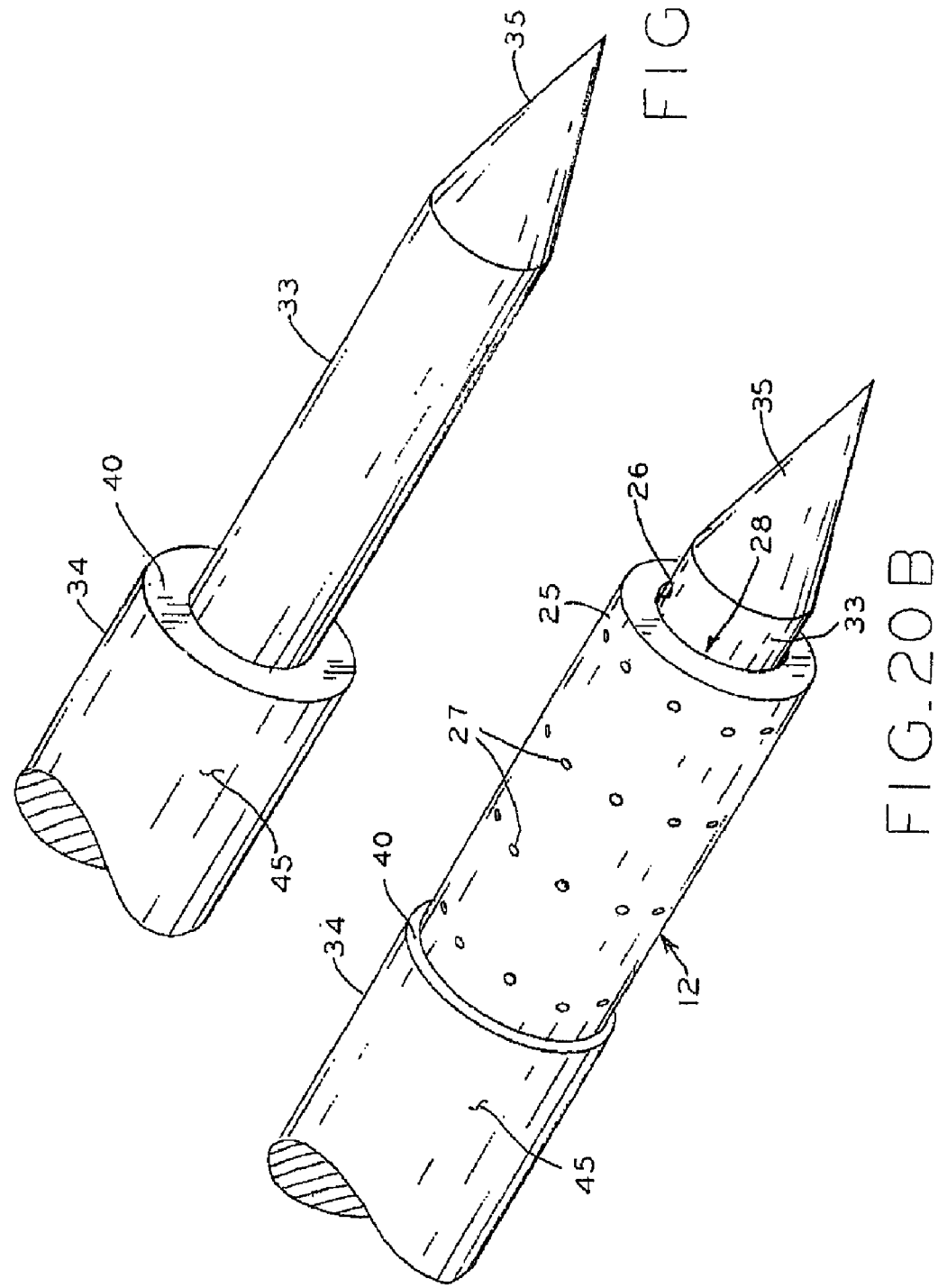

NON-DESTRUCTIVE TISSUE REPAIR AND REGENERATION

CROSS REFERENCE TO RELATED APPLICATIONS

This application is a continuation-in-part of co-pending U.S. patent application Ser. No. 10/558,926, filed Nov. 30, 2005, entitled Stent for Avascular Meniscal Repair and Regeneration, which is a U.S. nationalized patent application of PCT/US05/013973, filed Apr. 25, 2005, which claims priority to U.S. Provisional Patent Application No. 60/565,428 filed Apr. 26, 2004, the entire disclosures of which are hereby expressly incorporated by reference herein.

FIELD OF INVENTION

The present invention relates generally to surgical devices for repairing or regenerating body tissue and more specifically to surgical devices for repairing or regenerating soft tissues (i.e. articular cartilage, fibrocartilage, collagenous structures, ligaments, tendons, meniscus, spinal disc, TMJ disc etc. . . . ) of the joints (knee, hip, shoulder, temporomandibular joint, spine, fingers, ankle, toes, etc. . . . ), and to surgical methods using such devices.

BACKGROUND OF INVENTION

Meniscus tissue is comprised of a type of tissue known as fibrocartilage. Fibrocartilage is present in the form of a disc (spine, temporo-mandibular joint), meniscus (knee), labrum (shoulder, hip), etc. In the knee, as shown in FIG. 1, the meniscus is a semi-lunar, wedge shaped tissue that sits on top of the tibia and articulates with the tibia and femur during gait activities. It acts as a shock absorber between the femur and tibia and distributes the compressive and shear loads from the curved condyles of the femur to the relatively flat plateau of the tibia. Similar to articular cartilage, much of the meniscus is avascular and aneural. However, as shown in FIG. 2, the meniscus has three zones of vascularity: red zone, red/white zone, and white zone. The red zone refers to approximately the outer peripheral third of the meniscus. This zone is rich in blood supply. The white zone can be found in the approximate inner peripheral third of the meniscus and is void of blood supply, and the red/white zone can be found in the approximate middle third and has a limited blood supply.

Injuries and pathologies occur in the meniscus, labrum, and disc that manifest themselves in the forms of tears, as shown in FIG. 3, degeneration or other tissue defects. For the purposes of this document, "tissue defect" means any form of non-healthy tissue including, but not limited to, tissue tears, degenerative tissue, non-union bone fracture defects, or any other form of non-healthy tissue. Various types and degrees of tears and defects in the knee meniscus can and do occur often as a result of some twisting action in the knee or as a result of repetitive impact over time. Similar actions in the other joints can result in similar defects and tears in the similar structures present in those joints. Meniscus degeneration can also occur as a result of aging so that soft or hard areas develop in the tissue such that even common activities such as squatting can cause meniscal tears and defects.

Common surgical procedures for treating meniscal damage include repairing the tears and complete or partial meniscectomies. Repairing a tear is commonly performed when the tear is a longitudinal vertical tear in the vascular (or red) zone of the meniscus. The tear walls can be rasped or trephined to induce bleeding, especially when the tear is just beyond the borders of the red zone (i.e. in the red/white zone). The tear is stabilized with suture or some other repair device such that the relative motion of the tear faces is minimized or eliminated during load bearing. Also, the knee capsule tissue (i.e. synovium) is sometimes rasped to induce bleeding of this highly vascularized tissue into the joint with the intent to provide a better healing environment for meniscal tears. Many devices and surgical procedures exist for repairing meniscal tears by approximating the faces of the meniscal tear. Examples of such devices and procedures are disclosed in the following U.S. Pat. Nos. 6,319,271; 6,306,159; 6,306,156; 6,293,961; 6,156,044; 6,152,935; 6,056,778; 5,993,475; 5,980,524; 5,702,462; 5,569,252; 5,374,268; 5,320,633; and 4,873,976. The other common meniscal procedure, meniscectomy, involves the surgical removal of part of or all of the meniscus. Such procedures have commonly been performed in the case of "un-repairable" or complex tears such as radial tears, horizontal tears, vertical longitudinal tears outside the vascular zone, defibrillation, and/or degeneration. Defects that occur in the avascular (white) or limited vascular (red/white) areas typically do not heal. Meniscectomies typically provide immediate pain relief and restoration of knee function to the patient; however, with the absence of the meniscus, the long term effect on the knee can be cartilage wear on the condylar or tibial plateau surfaces and the eventual development of an arthritic condition such as osteoarthritis. Osteoarthritis is a result of cartilage degradation that is associated with chronic knee pain and often leads to total joint reconstruction. It is for these reasons that meniscal scaffolds and implants have been developed to regenerate or replace the tissue that is removed during a partial or total meniscectomy (see, for instance, U.S. Pat. Nos. 6,042,610; 5,735,903; 5,681,353; 5,108,438; 5,007,934; and 4,880,429).

Clinical experience indicates that white zone and red/white zone tears and defects typically do not heal even if they are stabilized with standard repair techniques. The option of not treating these types of defects is known to result in propagation of tears and defects and degeneration of the meniscus and subsequent degeneration of the articular cartilage and development of osteoarthritis. However, studies performed by Dr. Steven Arnoczky in animals [Arnoczky S P, Warren R F, Spivak J M; J Bone Joint Surg Am. 1988 Sep; 70(8):1209-17, "Meniscal repair using an exogenous fibrin clot. An experimental study in dogs."] and human clinical experience has shown that if the white or red/white zone defect surfaces are in contact with a blood clot (i.e. fibrin clot) then such tears or defects have a greater propensity to heal. So, if a surgeon were to deliver and fix a blood or fibrin clot to tear or defect surfaces, then healing would likely occur. Most surgeons, however, do not attempt to deliver and fix blood/fibrin clots to facilitate the repair of these types of tears because of the technical challenges. These meniscal procedures are typically performed using arthroscopic techniques (i.e. through small portals using an arthroscope or camera to visualize the surgical site). In order to see clearly through the arthroscope, the surgeon is required to constantly infuse the knee with fluid (i.e. saline solution, Ringer's solution, etc. . . . ); however, if he or she is trying to deliver a blood clot and fix it in the white or red/white zone defect, then the fluid would typically be turned off so that the clot does not disintegrate during the delivery and fixation stage. With the fluid turned off, the surgeon has the technical challenge of not being able to see the surgical site clearly; therefore, a technical dilemma exists: in order to see more clearly the fluid needs to be turned on, but in order to deliver and fix the clot the fluid needs to be turned off. Therefore, the technical challenges are too difficult to overcome in an arthroscopic environment; the surgeon therefore typically excises injured or degenerated white zone and red/white zone tissue (i.e. performs a partial or total meniscectomy). Performing these procedures in a non-arthroscopic setting (i.e. open condition) is not a viable option due to patient expectations, increased morbidity, and increased risks associated with larger incisions.

Currently, tissue engineering scaffolds are being developed to replace the meniscal tissue that has been removed, such as for instance, (ReGen Biologics' Collagen Meniscal Implant or CMI and DePuy's (a Johnson & Johnson company) small intestine submucosa meniscal implant. These implants are being developed to regenerate meniscal tissue; however, they are effective only when the implant is placed in direct contact with the vascular (red) zone of the meniscus. Therefore, if the defect area is confined to the avascular zone only, then one of the meniscal implants referred to above will not regenerate that tissue. For the defects that are confined to the avascular zone only, the surgeon must then remove only that portion of the meniscus that is injured and/or diseased and would not expand the defect into the vascular zone, thus removing "good tissue." So, for those patients with avascular zone defects, the only option today (and even in the future with the above mentioned tissue engineered scaffolds in their current configuration) is a partial meniscectomy with no tissue engineering replacement solution. Unfortunately for the patient who receives the partial meniscectomy, the long term prognosis includes chronic knee pain, break down of the articular cartilage, osteoarthritis, and even eventual total knee replacement.

Similar to the knee meniscus, other structures are found throughout the body that have avascular and vascular anatomies in close proximity where the avascular portion of these structures have very little propensity for healing. Some of these other structures are the labrum of the hip joint, the labrum of the shoulder joint, the meniscal-like structure of the wrist, the discs of the spine, the disc of the temporomandibular joint, diseased cardiac muscle (i.e. due to reduced blood flow from cardiovascular blockage) to name a few.

Also, in a spinal application, when a patient presents to a surgeon with a bulging or herniated or ruptured spinal disc, the adjacent vertebral bone is often sclerotic (i.e. thickened or denser). Since much of the nutrients for the spinal disc are delivered via diffusion through the vertebral endplates, the sclerotic bone could tend to decrease the amount of nutrients delivered to the disc, thus contributing to the diseased state of the disc.

SUMMARY OF THE INVENTION

The present invention is directed toward devices and surgical methods for repair and regeneration of diseased or damaged tissue such as the meniscus in the human knee joint. The devices and methods can also be applied toward the repair and regeneration of diseased or injured other fibrocartilage and tissues of the knee, hip, shoulder, temporo-mandibular joint (TMJ), spine, fingers, wrist, ankle, etc. While in many instances the current specification describes the repair and regeneration of tissue defects in a meniscus, the teachings of the present invention are applicable to tissue defects throughout the body.

The invention comprises, in one form thereof, a channel for blood, blood components, and cells to travel from a vascular area of tissue to an avascular or partially vascular area of tissue to facilitate healing and/or regeneration in these areas that would otherwise have a lower healing and regeneration capacity.

It is an objective of the present invention to provide a channel for blood, blood components and/or nutrients, and cells to travel from the vascular (red) zone such as in knee meniscus or synovium (i.e. knee capsule) to the avascular (white) or partially vascular (red/white) zone to facilitate healing and/or regeneration in these zones.

It is also an objective of the present invention to provide a biocompatible tube. The tube can have a stopping brim to prevent it from being inserted completely through the tissue. The tube is intended to be located within meniscal tissue such that it provides a channel from the vascular zone of the tissue (meniscus or synovium) to the avascular (white) or partially vascular (red/white) region. The tube wall can have openings, perforations, holes, or porosity that allow for blood, nutrients, and cells to enter the tube through the walls of the tube or stent. The tube wall exterior can be roughened or have protrusions or threads that will facilitate its fixation to tissue. The "tube" could be a cylinder with a porous configuration such that blood, nutrients, and cells could travel within and through the device.

It is also an objective of the present invention to provide a pathway through which blood, nutrients, and cells can pass to facilitate healing of an avascular (or partially vascular) tear/defect or to facilitate regeneration of avascular (or partially vascular) tissue when an implant is placed in addition to the tube(s) after performing a partial meniscectomy. In the case of a partial meniscectomy, the channel could function to deliver a blood or fibrin clot to the volume space of meniscus that was removed such that the clot acts as a scaffold in which cells can travel and propagate, thus, facilitating regeneration of that portion of the meniscus. In this case the open channel would also provide the access of the vascular area components to the in situ scaffold (i.e. blood or fibrin clot).

It is also an objective of the present invention to be comprised of a network of biocompatible tubes that are either attached to, integral with, or in close proximity to a meniscus implant. The implant is also comprised of a biocompatible material and can have interconnected porosity. The tube can have a stopping brim to prevent it from being inserted completely through the tissue. The meniscus implant/tube(s) device is located adjacent to avascular (white or red/white) meniscal tissue such that the tubes protrude into the meniscal tissue to or through the vascular tissue (meniscus or synovium). The tube(s) provides a channel from the vascular zone of the tissue (meniscus or synovium) to the avascular or partially vascular region into or onto the meniscus implant. This meniscus implant/tube(s) device(i.e. tubes integrated or attached to a scaffold) provides a pathway through which blood, nutrients, and cells can pass to the meniscus implant so that healing and regeneration of an avascular (or partially vascular) defect or tear can be accomplished. The tube portion of the meniscus/tube(s) device can have any or all of the same features as described in the tube device alone.

It is also an objective of the present invention to provide a method for repairing damaged or diseased fibrocartilage tissue (i.e. meniscus of the knee, labrum of the shoulder, acetabular labrum of the hip, articular disc of the wrist, spinal disc, temporomandibular disc, etc.). After locating the tear, degeneration or other defect in the avascular or partially vascular zone, one of two tasks can be performed. The tissue can be removed from the inner portion of the tear (i.e. perform a partial meniscectomy) or the tear can be repaired using a number of standard repair techniques (vertical or horizontal mattress suturing, Mitek's RapidLoc™ Meniscal Repair Device for the meniscus, Bionx Arrow™ for the meniscus, etc.). If a partial meniscectomy is to be performed followed by implantation of a meniscus regenerating or replacing device or implant, then the stent can be placed into the remnant native meniscal tissue such that it provides an open channel through which blood, nutrients, and cells can flow from the vascular region of the tissue to the implant, thus facilitating healing or regeneration. After a partial meniscectomy, a meniscus/tube(s) device (i.e. tubes integrated or attached to a scaffold) could be implanted and fixed to the remaining native meniscal tissue such that the tube portion of the device protrudes into and/or through the vascular zone of the meniscus and/or synovium. The delivery of the meniscus/tube(s) device could be accomplished arthroscopically with standard techniques. The fixation could be accomplished arthroscopically as well using standard devices and techniques (suture, meniscal repair devices such as DePuy Mitek's RapidLoc, Linvatec's Bionx Arrow, etc.). If the tear is to be repaired (instead of removing the tissue via a partial meniscectomy), then the stent can be arthroscopically placed either using an all inside or inside-out technique from the outer tear surface to or through the vascular region (providing a channel) or through both tear surfaces to the vascular region (providing a channel and a fixation for the tear), thus, facilitating repair of the avascular or partially vascular tear. Alternatively, the stent could be arthroscopically delivered using an outside-in technique.

It is also an objective of the present invention to provide a method for delivering biological treatments [i.e. blood, blood components, platelet rich plasma, tissue, bone marrow, bone marrow components, stem cells, fibroblast cells, synoviocyte cells, other cells, angiogenic factors (new blood vessel formation growth factors such as VEGF, IGF, etc. . . . ), other growth factors, hyaluronic acid, gene therapies, other biologic molecules etc.], drugs [analgesic, anti-clotting, clotting, anti-inflammatory, anti-infectives, etc. . . . ], and other substances to the tear or defect area through the tube. After the tube device is positioned or during/before the insertion process, a substance could be delivered through the tube either to the tear/defect area or to the vascular area. The substance could enhance or initiate healing, increase blood flow, improve angiogenesis, induce clotting in the duct and tear/defect, deliver cells, deliver growth factors, deliver biologic elements, etc.

It is also an objective of the present invention to provide devices as mentioned above that would be used in other joints of the body such as the hip, the wrist, the shoulder, the ankle, fingers, the toes, the spine, the temporomandibular joint, etc.

It is also an objective of the present invention to provide devices as mentioned above that would be used in cardiac muscle. For instance, if the cardiac arteries are diseased and/or blocked to the point where the cardiac muscle is starved for blood and nutrients, a tube(s) could be implanted into the cardiac muscle such that blood is delivered to the compromised cardiac muscle from an area where vascularity is more abundant.

It is also an objective of the present invention to be comprised of a channel for blood, blood components, and cells to travel from a vascular area of bone to an avascular or partially vascular area, such as articular cartilage, to facilitate healing and/or regeneration in these areas that would otherwise have a lower healing and regeneration capacity. For instance, when a surgeon encounters a patient with osteochondritis dessicans (OCD), the typical surgical treatment is to remove the cartilage defect or flap and then proceed to microfracture or microdrill the subchondral bone to induce bleeding and provide a pathway for bone marrow components to aid in the healing of the OCD lesion. The surgeon, in addition to or instead of microfracturing and microdrilling, could insert one or more stents that would retain the channel into the bone such that blood and marrow components and cells could have access to the OCD lesion, thus, improving the healing capacity of that tissue site. Also, in a spinal application, when a patient presents to a surgeon with a bulging or herniated or ruptured spinal disc, often the adjacent vertebral bone is sclerotic (i.e. thickened or more dense) and can impede the nutrient flow from the vertebral bone to the spinal disc. Therefore, the surgeon could insert one or more stents into the vertebral bone such that an open channel is created from the vertebral bone to the disc space. Alternatively, the surgeon could insert the stents into the periphery of the disc, through the outer capsule such that the capsular vascularity would have access to the spinal disc interior. This latter procedure could be performed using techniques similar to an epidural procedure.

BRIEF DESCRIPTION OF DRAWINGS

The above mentioned and other features and objects of this invention, and the manner of attaining them, will become more apparent and the invention itself will be better understood by reference to the following description of embodiments of the invention taken in conjunction with the accompanying drawings, wherein:

FIG. 1 shows a normal meniscus;

FIG. 2 shows a cross sectional view of a normal meniscus;

FIG. 9 shows a cross sectional view along line 9-9 of the meniscus of FIG. 8;

FIG. 10 shows the meniscus of FIG. 9 with a stent placed therein;

FIG. 11 shows the meniscus of FIG. 9 with a stent with a stopping brim placed therein;

FIG. 12 shows a cross sectional view along line 9-9 of the meniscus of FIG. 8 with a stent and an implant or regeneration device;

FIG. 13A shows a perspective view of a stent in the shape of a cylindrical tube;

FIG. 13B shows a perspective view of a stent in the shape of a cylindrical porous rod;

FIG. 14 shows a perspective view of a stent in the shape of a cylindrical tube with a stopping brim;

FIG. 15 shows a perspective view of a stent in the shape of a cylindrical tube with external circumferential ribs;

FIG. 16A shows a perspective view of a stent in the shape of a cylindrical tube with external threads 37;

FIG. 16B shows a perspective view of a stent in the shape of a cylindrical tube with external threads having a variable pitch;

FIG. 17 shows an elevational view of another embodiment of a stent in the shape of a cylindrical tube with external circumferential fins;

FIG. 18 shows a perspective view of a stent in the shape of a cylindrical tube with external longitudinal ribs;

FIG. 19 shows an end view of the stent of FIG. 16A;

FIG. 20A shows a perspective view of a driver that is used to deliver a stent into tissue;

FIG. 20B shows a perspective view of a driver with the stent of FIG. 13A loaded onto it;

Figure 3:
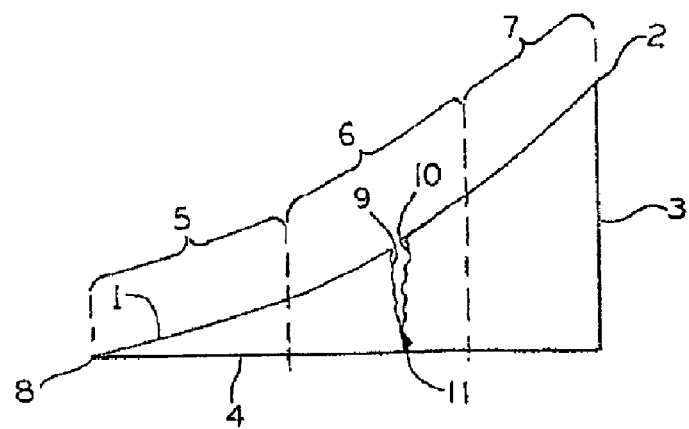
FIG. 3 shows a cross sectional view of a meniscus showing a vertical tear in the red/white zone.

Corresponding reference characters indicate corresponding parts throughout the several views. Although the exemplifications set out herein illustrate embodiments of the invention, in several forms, the embodiments disclosed below are not intended to be exhaustive or to be construed as limiting the scope of the invention to the precise forms disclosed.

DETAILED DESCRIPTION OF THE ILLUSTRATED EMBODIMENTS

FIG. 1 shows a view of a normal meniscus. The meniscus has a triangular cross section as shown in FIG. 2. The top of the articulating surface 1 interfaces with the femoral condyle and the bottom of the articulating surface 4 interfaces with the tibial plateau. The inner edge 8 and the outer rim 2 are indicated in the figure. The outer wall 3 defines the outermost boundary of the meniscus tissue.

FIG. 2 shows a cross sectional view of a normal meniscus showing approximate locations of the vascular (red) zone 7, avascular (white) zone 5, and partially vascular (red/white) zone 6 in an adult human.

FIG. 3 shows a cross sectional view of a meniscus with a vertical tear 11 in the red/white zone 6. The inner and outer tear faces, 9 and 10, are indicated in this figure.

Figure 4:
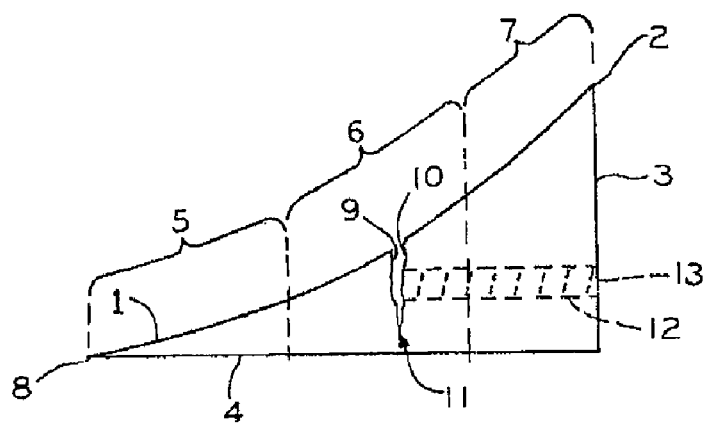
FIG. 4 shows a cross sectional view of a meniscus showing a vertical tear in the red/white zone with a stent inserted.

FIG. 4 shows a cross sectional view of a meniscus with a vertical tear 11 in the red/white zone 6 with a stent 12 inserted at the outer tear face 10 through the vascular (red) zone 7. The tear 11 has not yet been repaired in this figure. The outer opening 13 of the stent 12 in this example is located at the meniscus outer wall 3; therefore, the stent outer opening 13 would be positioned at the interface of the meniscus and synovium (or capsule) of the knee (See FIG. 28: items 47 & 52).

Figure 5:
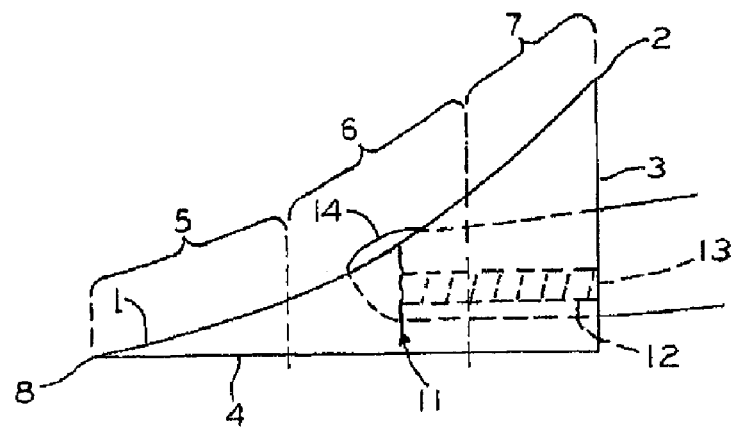
FIG. 5 shows a cross sectional view of a meniscus showing a vertical tear in the red/white zone with a stent inserted and the tear repaired.

FIG. 5 shows a cross sectional view of a meniscus which has a vertical tear 11 in the red/white zone 6 with a stent 12 inserted at the outer tear face 10 through the vascular (red) zone 7. The tear 11 has been repaired using a vertical mattress suture 14 technique.

Figure 6:
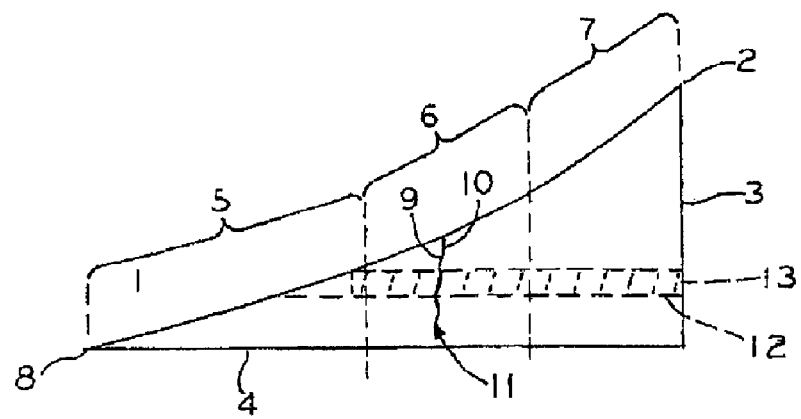
FIG. 6 shows a cross sectional view of a meniscus showing a vertical tear in the red/white zone with an inserted stent acting as a fixation device.

FIG. 6 shows a cross sectional view of a meniscus with a vertical tear 11 in the red/white zone 6 with a stent 12 inserted through both tear surfaces (9 & 10) from the avascular (white) zone 5 through the vascular (red) zone 7. In this example, the stent 12 acts as a tube to provide a pathway for blood, nutrients, cells, etc. . . . from the vascular area 7 to the partially vascular area and also acts as a fixation device to approximate the inner 9 and outer 10 tear faces together. Therefore, in this example, the blood, nutrients, cells, etc. . . . facilitate the biological healing. The fixation device also mechanically holds the inner 9 and outer 10 tear surfaces together so that healing can occur.

Figure 7:
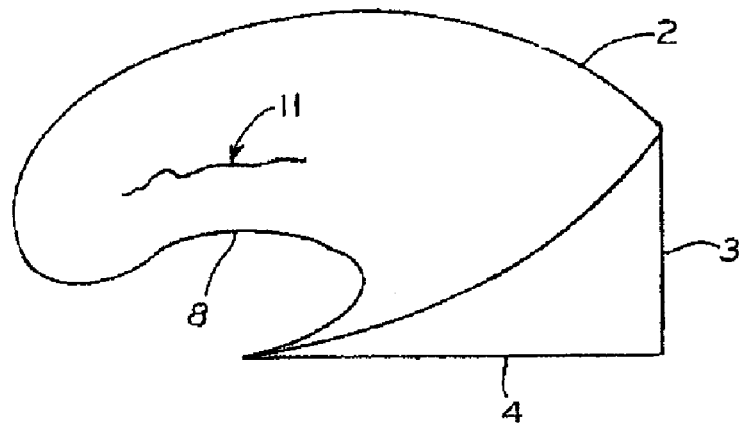
FIG. 7 shows a meniscus with a vertical tear.

FIG. 7 shows a view of a meniscus with a vertical tear 11 in the avascular (white) 5 or partially vascular (red/white) zone 6 of the meniscus. The inner edge 8 and outer rim 2 of the meniscus are indicated in this figure for orientation purposes.

Figure 8:
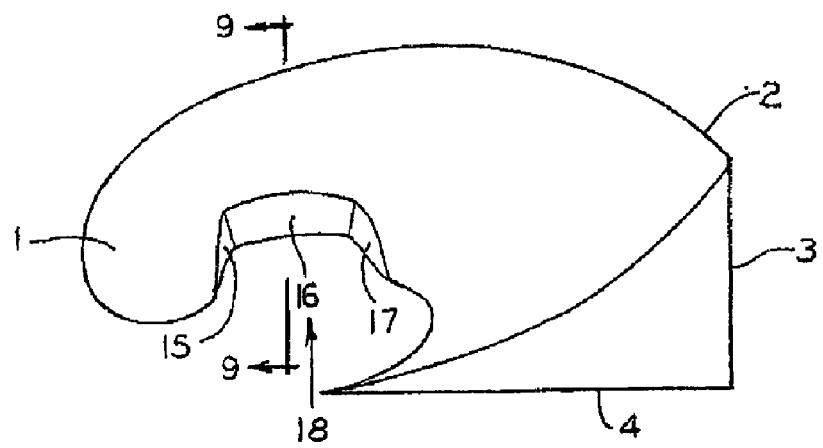
FIG. 8 shows a meniscus with the tissue that is on the inner side of the avascular or partially vascular tear removed, i.e., with a partial meniscectomy.

FIG. 8 shows a view of a meniscus with the tissue, which is located on the inner side of the avascular or partially vascular tear, removed (i.e. partial meniscectomy performed). The posterior 15, anterior 17 and outer 16 walls define the defect 18 created by the partial meniscectomy procedure. This figure represents the standard of care given by an orthopaedic surgeon to a patient with a tear or defective tissue in the avascular 5 or partially vascular 6 zone of the knee meniscus.

FIG. 9 shows a cross sectional view of a meniscus that has the inner side of the avascular or partially vascular tear 11 removed as indicated by lines 9-9 of FIG. 8.

FIG. 10 shows a cross sectional view of the meniscus after a partial meniscectomy (similar to FIG. 9) except that a stent 12 has been inserted to reach from the avascular (white) 5 or partially vascular (red/white) 6 tear face(s) (9 & 10) to or through the vascular (red) zone 7 of the meniscus to or into the synovium of the knee. In this example, the stent 12 would act to provide a channel through which blood could flow and eventually clot, creating a naturally derived scaffold with biological factors in which cells can travel, reside, and thrive. The channel which would also have blood clotted in it would provide a pathway through which cells from the outer region could find their way to the scaffold. This combination of blood clot, biological factors, and cells would provide the proper environment for that portion of the meniscus that was removed to be regenerated.

FIG. 11 shows a cross sectional view of the meniscus after a partial meniscectomy with a stent 12 in place (similar to FIG. 10) except the stent 12 has a stopping brim 29 to impede or prevent it from advancing outwardly.

FIG. 12 shows a cross sectional view of the meniscus that has the inner side of the avascular (white) or partially vascular (red/white) tear removed (partial meniscectomy). A stent 12 that has been inserted to reach from the avascular (white) 5 or partially vascular (red/white) 6 tear face 9 to the vascular (red) zone 7. An implant or regeneration device 20 is fixed against the face 10 of the remaining meniscus such that the stent opening interfaces with the implant or device 20.

Figure 28:
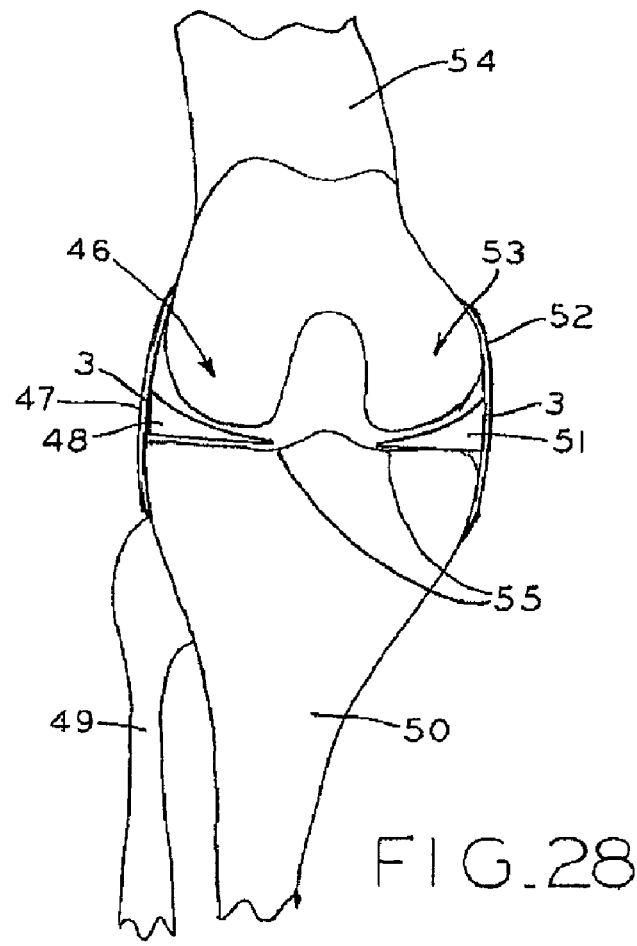
FIG. 28 shows a perspective view of a knee cross section showing some of the major structures.

For orientation, FIG. 28 shows a perspective view of a knee cross section showing some of the major structures. The fibula 49 and tibia 50 bones comprise the lower leg thigh bones; whereas, the femur 54 is the upper leg or thigh bone. The medial meniscus 51 and lateral meniscus 55 are indicated in cross section beneath the medial condyle 52 and lateral condyle 46, respectively, and above the tibial plateau 55. The outer wall 3 of the medial 51 and lateral 47 menisci are in contact with the medial synovium (or knee capsule) 52 and lateral synovium (or knee capsule) 47, respectively.

A variety of stents 12 utilizing the principles of the present invention are illustrated in the following drawings. The illustrated stents 12 are intended for implantation in a patient for channeling blood and/or nutrients from a vascularized area 7 of the tissue to a non- (5) or less 6 vascularized area of the tissue, thus, facilitating repair of that non- 5 or less 6 vascularized tissue of the body in the patient. The illustrated embodiments would most commonly be used in repairing meniscus tissue of the knee; however, the invention is not so limited. As used herein, the term stent refers to a device that is composed of a biocompatible (bioabsorbable or non-absorbable) material and has an open channel 28 that acts to route blood, nutrients, and/or cells from a vascular area 7 to an area that is not as vascularized (5, 6). The open channel is not required to be a through hole or unimpeded lumen 28. The open channel could be accomplished via interconnective porosity present in a biocompatible material that is configured in the shape of a stent 12 (FIG. 13B). The stent 12 acts to maintain the hole (or a channel or separation of tissue) in the tissue for a time so that blood or nutrients can be supplied to a limited vascular area to facilitate healing.

As used herein, bioresorbable, resorbable, bioabsorbable, and absorbable are intended to be interchangeable. All four terms are intended to mean materials that are naturally degradable in vivo over time. All are intended to include both natural and man-made materials and to include new materials, as they are developed, unless a specific material or a type of material are identified. Bioabsorbable materials useful for creating stents of the present invention include polyesters; poly-L-lactic acid (PLLA); polyglycolic acid (PGA); polydioxinone (PDS or PDO); polycaprilactone (PCL); polyvinyl alcohol (PVA); polyethylene oxide (PEO); poly(trimethylene carbonate): polymers disclosed in U.S. Pat. Nos. 6,333,029 and 6,355,699, the disclosures of which are hereby expressly incorporated by reference herein; polymers derived from tyrosine; polymers derived from chitosan; small intestine submucosa (SIS), urinary bladder submucosa, materials derived from collagenous tissues.

Referring now to FIG. 13A, the stent 12 is shown composed of a tube with an outer surface 25, an inner surface 26, and a through lumen 28. The stent 12 is ideally 2 cm or less in length but could be longer, depending on the distance between the tear or defect 11 and the vascular area 7 from which the blood, nutrients, and cells will come. The inner diameter or dimension of the lumen 28 is ideally in the 0.5 to 3.0 mm range and can be either larger or smaller depending on the actual tissue in which it is implanted. The wall thickness of the stent is ideally in the 0.1-1.0 mm but could be thicker or thinner as required due to the loads induced by the surrounding tissue and biomechanics. Additionally holes 27 through the outer surface 25 and inner surface 26 can be provided. The purpose of the holes 27 is to provide access ports through which blood and nutrients can flow from a vascularized area 7, as shown in FIGS. 2-6, into the stent 12. These holes 27 could be in the form of porosity or discrete holes. Ideally the hole 27 diameter will be in the 0.05 to 1.0 mm range but could be larger or smaller depending on the tissue type, desired cell types, nutrients, etc. . . that one wishes to enter and/or exit through holes 27. Note that holes 27 do not necessarily have to be round or square or elliptical or any consistent geometry in particular but rather could be in the form of various pores of various shapes and geometries. In the case of porosity, the ideal size is in the 10 to 5000 micron range and this porosity could be either through porosity or interconnective porosity. The exit/entrance ends 13 of through lumen 28 also provides an access port through which blood, nutrients, and cells can travel to areas of less vasculature 6 or no vasculature 5, as shown in FIGS. 2-6. These access ports 27 and 28 also provide entrance and exit pathways for cells to thrive. Note that the stents 12 shown in FIGS. 13A and 14-18 could exist without a through lumen 28. Instead, the stent 12 could be a solid appearing cylinder with porosity throughout the structure as shown in FIG. 13B. The porosity could be in the form of discrete holes that are interconnected or in the form of interconnective porosity. This same structure could be accomplished by inserting a porous cylinder into the through lumen 28 of the stent 12 shown in FIGS. 13A and 14-18 either before or after insertion of the stent 12 into tissue. Note that the outer surface 25 of the stent 12 can be smooth or can be roughened to aid in fixation of stent 12, and to increase surface area contact of stent 12 with native tissue. The roughened outer surface 25 can also act as a rasp during insertion to increase the amount of bleeding and, thus, expose more vasculature in the vascular area 7 and/or the partially vascular area 6 of the tissue.

The stent 12 illustrated in FIG. 13B is similar to stent 12 of FIG. 13A but is a porous rod. The porosity 47 can be accomplished through mechanical means (i.e. drilling, stabbing, picking, etc. . . . ) or through material means (i.e. interconnective porous material, lyophilization of slurry material, etc. . . . ) or through other means (i.e. 3-D printing, etc. . . . ). The ideal size of the pores is in the 10 to 5000 micron range. The porosity allows for blood, nutrients, and cells to travel through the stent 12 from an area of vascularity to an area of limited or no vascularity, thus, facilitating healing of the limited or no vascular tissue.

The stent 12 illustrated in FIG. 14 is similar to stent 12 of FIG. 13A but also has a stopping brim 29 so that the stent 12 can be inserted into tissue only a predetermined distance as illustrated in FIG. 11. Thus, the brim 29 would impede the stent 12 from traversing further into the tissue. The brim 29 could be circular, square, rectangular, trapezoidal, elliptical, scalloped, segmented, etc. . . . and is required to be larger than the dimension of the outer surface 25 of the stent 12. The brim 29 as indicated in FIG. 14 is ideally 0.5-2.0 mm larger than the outer surface 25 dimension and is ideally 0.05-1.0 mm thick. This impedance function could be accomplished by a gradual transition from the smaller outer surface 25 dimension to the brim 29 dimension (i.e. ramping up from the outer surface 25 to the outer brim 29). In this case, the ramp transition could happen over a length along the long axis of the stent 12 of 1-10 mm ideally but could occur over a shorter or longer length.

FIG. 15 shows a stent 12 with external circumferential ribs 36 which help with fixation of stent 12 in tissue. The tissue has elasticity associated with its material properties so that the tissue will somewhat conform to the outer geometry of the stent 12 after insertion; therefore, the external circumferential ribs 36 will become imbedded into the tissue, thus, impeding the stent 12 from moving once positioned. Tissue also has a material property commonly referred to as viscoelasticity. The tissue, therefore, will, with time, conform to the outer geometry of the stent even more. The plurality of external circumferential ribs 36 could be one or more ribs. FIG. 15 indicates four external circumferential ribs 36. The spacing between ribs 36 is ideally 2-10 mm; however, it could be more or less, depending on the tissue, the application, and the other dimensions of the ribs 36. Ideally the external circumferential ribs 36 extend radially outwardly from the outer surface 25 by 0.1-2.0 mm; however, they could extend to a greater or lesser amount as well. The axial width of the ribs 36 ideally will be in the 0.1-2.0 mm range but, again, could be wider or narrower, depending on the specific application. Also, the plurality of external circumferential ribs 36 that are shown in this figure are not required to share common dimensions. Stent 12 includes an outer diameter defined by outer surface 25 and the radially outward extent of ribs 36. The outer diameter defined at ribs 36 comprises the largest value of the outer diameter of stent 12, while the other diameter defined by outer surface 25 defines the smallest value of the outer diameter of stent 12. In one exemplary embodiment of the present invention, the end of the stent 12 utilized in accordance with the present invention that is positioned adjacent to a tissue defect will have an outer diameter value that is less than the largest outer diameter of the stent, e.g., the outer diameter defined by ribs 36. In certain exemplary embodiments, the stent will have its smallest outer diameter at the end position adjacent to the tissue defect.

FIG. 16A shows a stent 12 with external threads 37 which help with fixation of stent 12. Unlike FIG. 15, stent 12 indicated in FIG. 16A can be turned or screwed into the tissue as opposed to pushed into the tissue as with the stent 12 of FIG. 15 with circumferential ribs 36. The thread pitch or the number of threads 37 per mm or per inch can vary, depending on tissue type, other dimensions, and application, to name a few. Either a "coarse" or "fine" thread spacing could be used effectively in the stent. Ideally the external threads 37 extend from the outer surface 25 by 0.1-2.0 mm; however, they could extend to a greater or lesser amount as well. The axial width of the ribs 13 ideally will be in the 0.1-2.0 mm range but, again, could be wider or narrower, depending on the specific application. A variable pitch could also be applied to the stent 12 as shown in FIG. 16B, especially for the application indicated in FIG. 6 where the stent 12 also acts as a fixation device to pull and retain the tear 11 faces (9, 10) together. The variable pitch thread 37 could be used to ensure that the two faces (9, 10) of the tear 11 are pushed together after implantation of the stent 12. The variable pitch would include smaller thread spacing at one end of the stent 12 with larger thread spacing on the opposite end. This variable pitch would tend to pull the two surfaces (9, 10) of the tear 11 together. Threads 37 may terminate before an end of stent 12 in certain embodiments. In these embodiments, the end of stent 12 that does not include threads can be positioned adjacent to the tissue defect as described above. In the case of a meniscal tear, configuring stent 12 to have a smaller outer diameter at the location of a meniscal tear is useful because the meniscus will likely be thinner adjacent to the tear location and thicker in the vascular area in which the opposite end of the stent is positioned.

Figure 24:
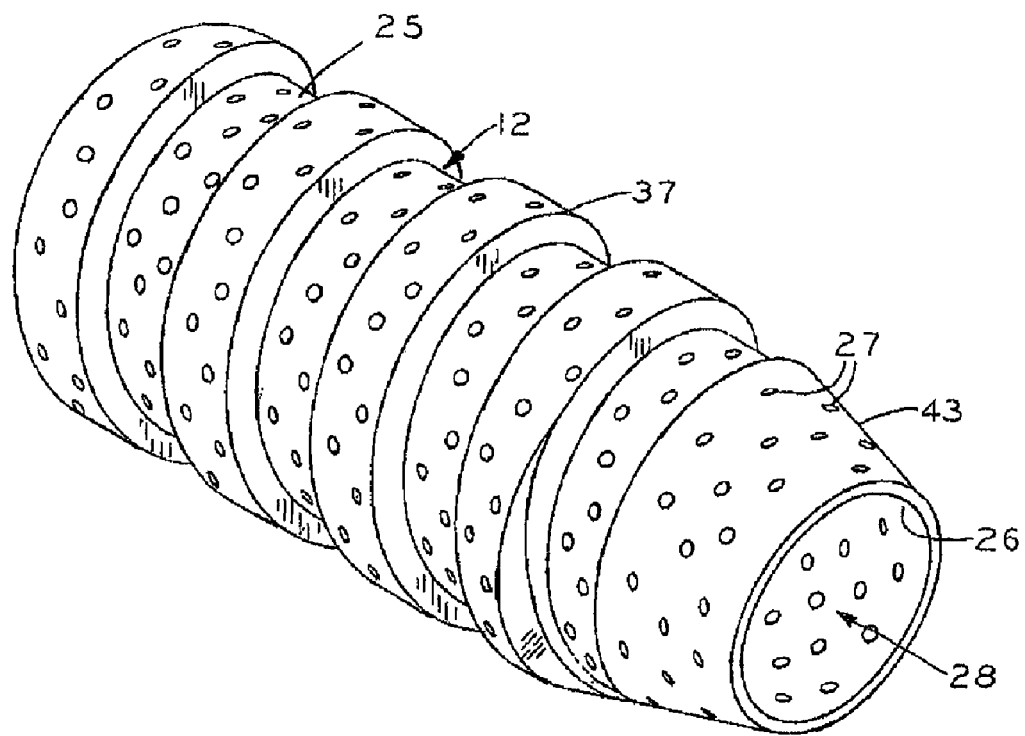
FIG. 24 shows a view of the stent of FIG. 16A having a lead in chamfer.

FIG. 24 shows an isometric view of the type of stent indicated in FIG. 16A. Note that the stent 12 in FIG. 24 has an added feature of a lead in chamfer 43. This chamfer 43 provides less resistance into the tissue than a blunt end as shown in FIG. 16A or 16B; therefore, with the stent 12 of FIG. 24 insertion will be easier to initiate into tissue. FIG. 19 shows a cross section 40 of the stents 12 of FIGS. 16 and 24. The non-circular cross section 40 could be used to drive the stent device 12 into tissue with a driver that has a similar cross section.

Figure 25:
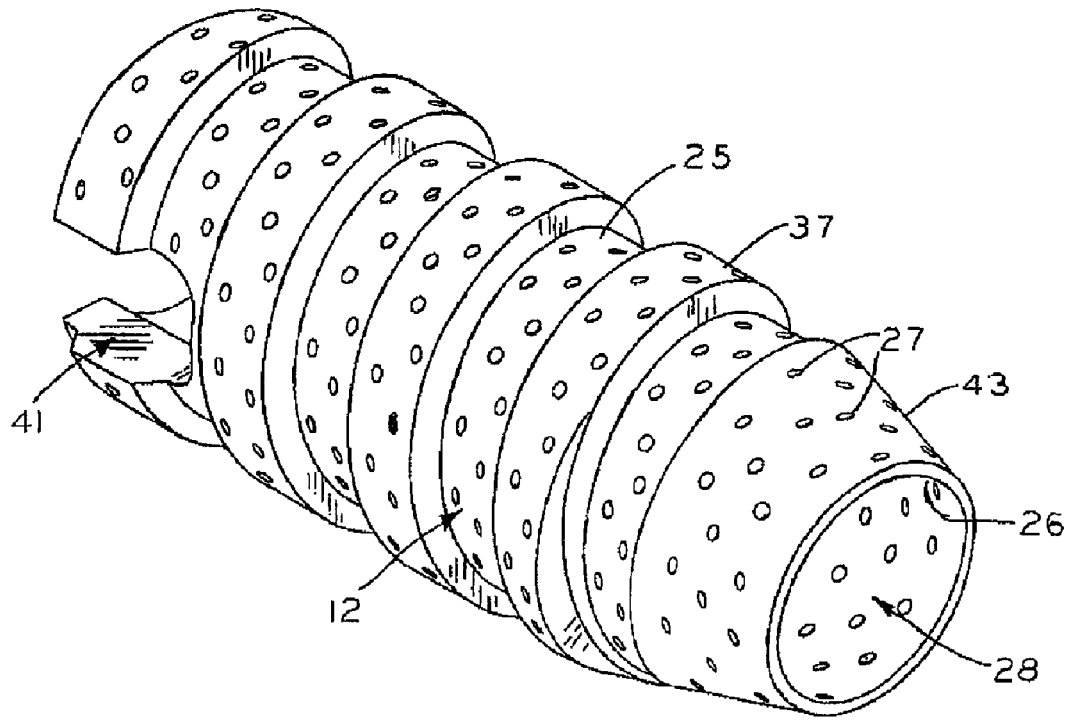
FIG. 25 shows a perspective view of the stent of FIG. 24 having a driver slot in the back end of the stent.
Figure 26:
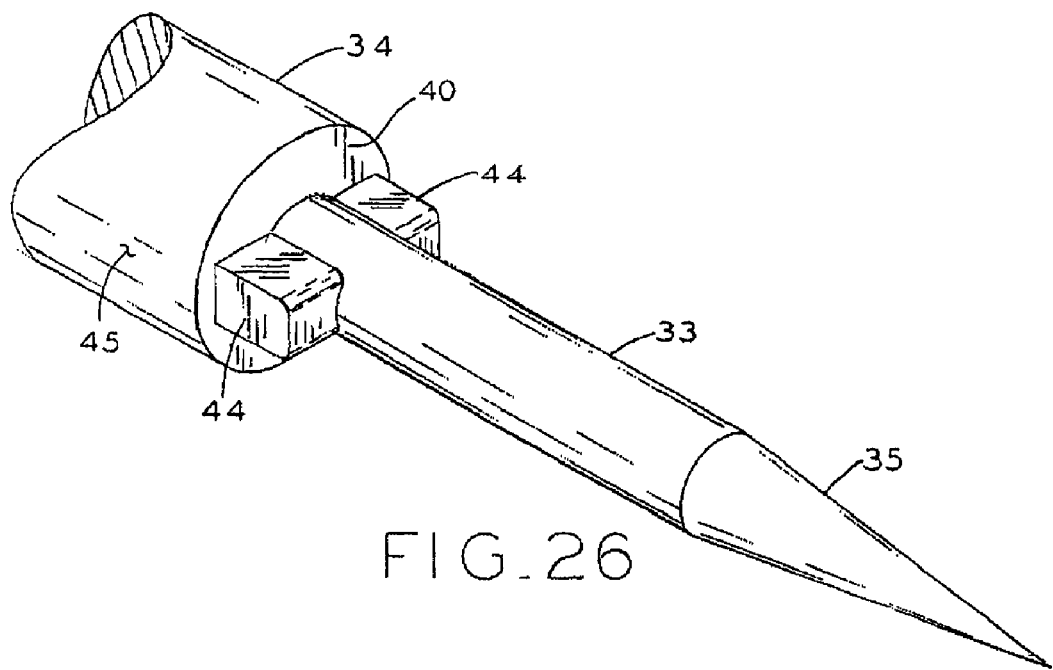
FIG. 26 shows a perspective view of a driver with raised bosses.
Figure 27:
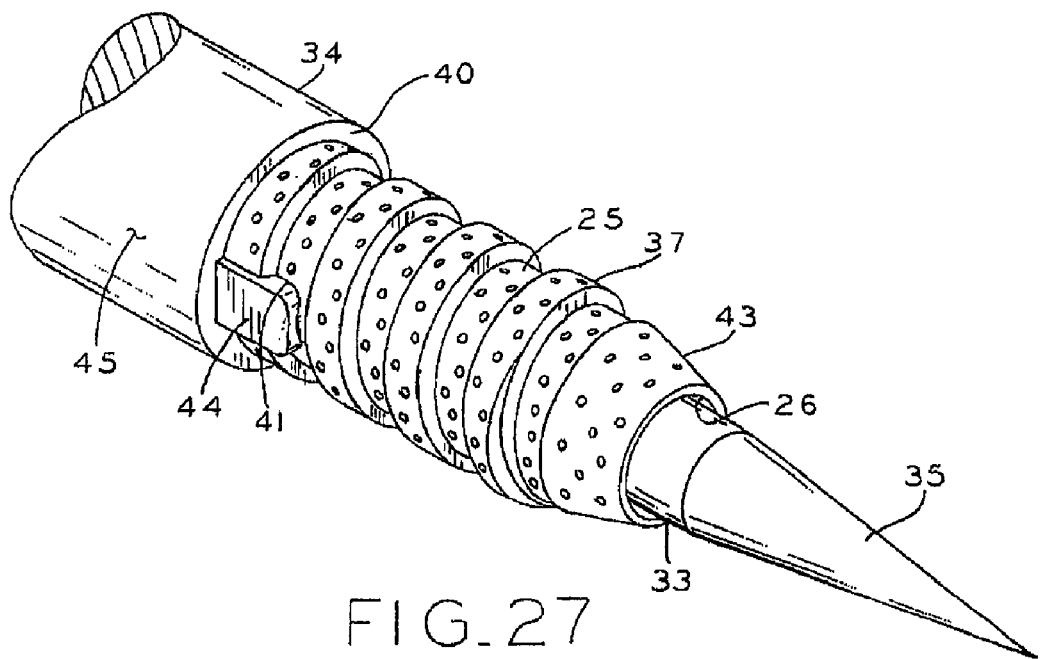
FIG. 27 shows a perspective view of the slotted stent of FIG. 25 and the slot driver of FIG. 26 in the loaded condition, ready for insertion into tissue.

In FIG. 19, the internal cross section of the stent 12 is shown as a square or rectangle. The internal cross section could be any non-circular geometry (i.e. square, rectangle, triangle, trapezoidal, elliptical, hexagonal, star, circular with a key slot, etc. . . . ). The matching geometry of a driver 45 would be used to torque the stent 12 into the tissue. FIG. 25 shows a slotted 41 version of a threaded stent. The slot 42 interfaces with the raised boss 44 of the driver 45 indicated in FIGS. 26 and 27.

A surgeon could insert the sharpened tip 35 of the driver 45 shown in FIG. 20A, followed by the lead in chamfer 43 of the stent 12 of FIG. 24. As the surgeon turned the driver 45, the threads 37 would interface with the tissue and screw the stent 12 into the tissue. After delivery of the stent, the driver 45 could be pulled out of the stent 12 and knee joint, thus, leaving the stent 12 behind in the tissue. In this way, the stent can be inserted into the tissue by separating the tissue to provide an access for the stent without removing or ablating the tissue.

FIG. 17 shows a stent 12 with external circumferential fins 38 which help with fixation into the tissue. The difference between the fins 38 and the ribs 36 is essentially the edge geometry. Where the rib 36 configuration impedes forward and backward motion equally, the configuration of fin 38 impedes motion opposite to the insertion direction. The insertion direction is indicated by the arrow 46. In other words, the fin 38 geometry is configured such that insertion of the stent 12 into tissue requires less force than removal of the stent 12 from tissue in the opposite direction from the insertion direction. The fin geometry is configured such that the forward side of fin 38 is ramped up from the outer surface 25 and back such that as the stent 12 is inserted into the tissue, the fin 38 flexes back; however, if a force in the opposite direction of the insertion force is applied to the stent 12, then the fin 38 "digs" into the tissue to resist that force and, thus, resist motion of the stent 12 in that direction. As explained in connection with the circumferential rib 36 embodiment of FIG. 15, the tissue has elasticity associated with its material properties so that the tissue will somewhat conform to the outer geometry of the stent 12 after insertion; therefore, the fins 38 will become imbedded into the tissue, thus, impeding the stent 12 from moving once positioned, especially in the direction opposite to the direction of insertion. The tissue also has a material property commonly referred to as viscoelasticity. The tissue, therefore, will conform to the outer geometry of the stent even more with time. The plurality of external circumferential fins 38 could be one or more fins. This figure indicates three external circumferential fins 38. The spacing between fins 38 is ideally 2-10 mm; however, it could be more or less, depending on the tissue, the application, and the other dimensions of the fins 38. Ideally the external circumferential fins 38 extend from the outer surface 25 by 0.1-2.0 mm; however, they could extend to a greater or lesser amount as well. The axial width of the fins 38 ideally will be in the 0.1-2.0 mm range but, again, could be wider or narrow, depending on the specific application. Also, the plurality of external circumferential fins 38 that are shown in this figure are not required to share common dimensions.

FIG. 18 shows external longitudinal ribs 39 which help with fixation of stent 12. The purpose of these longitudinal ribs 39 is to resist rotation of the stent 12 about the long axis of stent 12. Since the tissue is elastic, it will somewhat conform to the outer geometry of the stent 12 after insertion; therefore, the longitudinal ribs 39 will become imbedded into the tissue, thus, impeding the stent 12 from rotating. The tissue's viscoelasticity will cause the tissue to conform to the outer geometry of the stent even more with time. The plurality of external longitudinal ribs 39 could be one or more ribs. This figure indicates four external longitudinal ribs 39. The circumferential spacing between the ribs 39 is ideally equally spaced (in this case 90 degrees apart); however, it could be more or less, depending on the tissue, the application, and the other dimensions of the ribs 39. Ideally the external longitudinal ribs 39 extend from the outer surface 25 by 0.1-2.0 mm; however, they could extend to a greater or lesser amount as well. The circumferential width of the ribs 39 ideally will be in the 0.1-2.0 mm range but, again, could be wider or narrow, depending on the specific application. The profile of the ribs 39 does not necessarily need to be consistent from end to end. In fact, the leading edge of the rib 39 may be ramped as shown in FIG. 18 so that insertion of the stent 12 may be made easier. Also, the plurality of external longitudinal ribs 39 that are shown in this figure are not required to share common dimensions.

Figure 21:
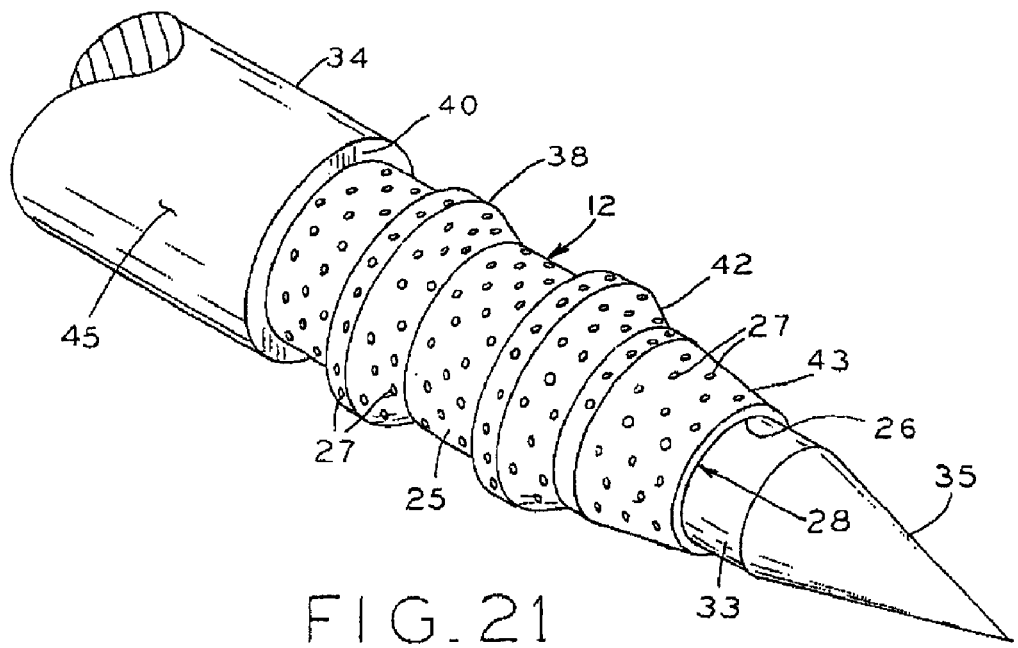
FIG. 21 shows a perspective view of a driver with the stent of FIG. 17 loaded onto it.
Figure 22:
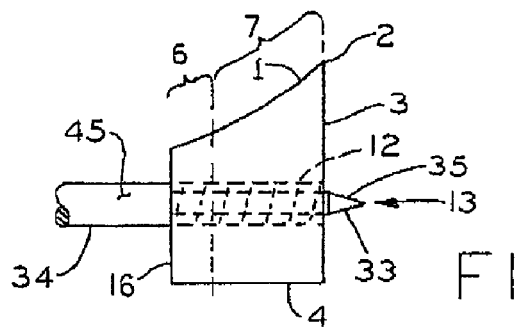
FIG. 22 shows a perspective view of a driver with a stent being delivered into tissue.
Figure 23:
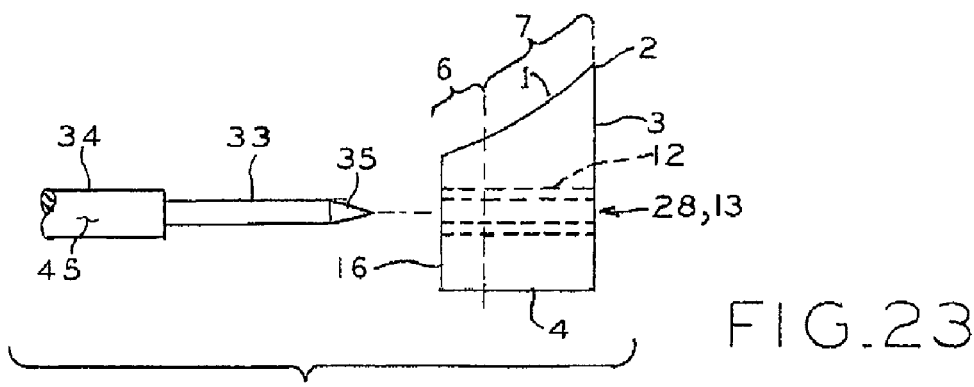
FIG. 23 shows a perspective view of a driver with a delivery needle after delivering a stent into tissue.

FIG. 20A shows a driver 45 that could be used to insert a stent 12. A surgeon could insert the sharpened tip 35 of delivery needle 33 of driver 45, followed by the stent 12 as shown in FIG. 20B or FIG. 21. As the surgeon pushed on the driver 45, the stent 12 would travel into the tissue as shown in FIG. 22. As shown in FIG. 22, in certain embodiments of the present invention, the step of inserting the stent into the meniscus comprises inserting stent 12 into the meniscus through tissue defect 16. After delivery of the stent, the driver 45 could be pulled out of the stent 12 and knee joint, thus, leaving the stent 12 behind in the tissue as shown in FIG. 23.

Figure 30:
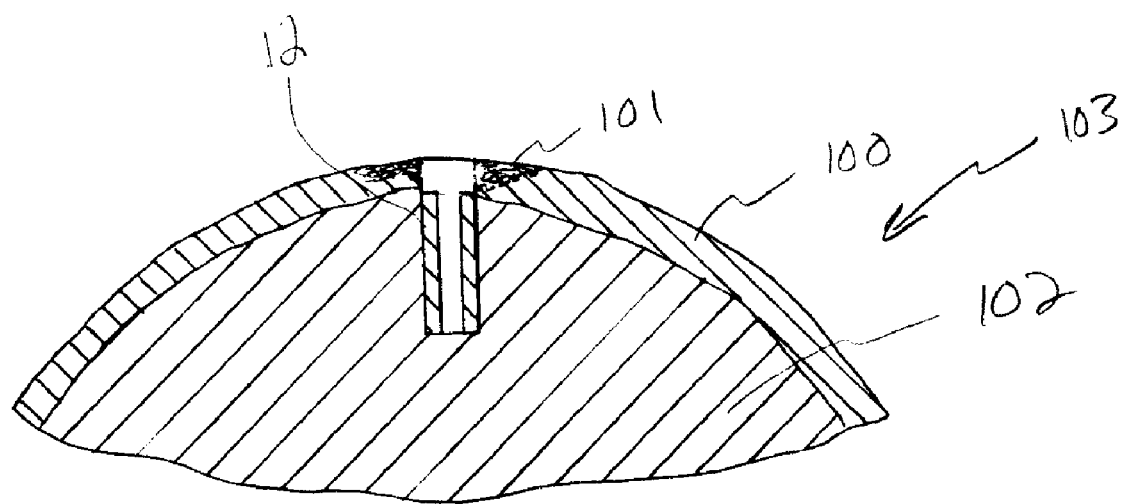
FIG. 30 is a partial sectional view of a bone with a stent positioned therein.

FIG. 30 illustrates stent 12 positioned in bone 103, with one end of stent 12 terminating at tissue defect 101 formed in cartilage 100. In this position, the opposite end of stent 12 reaches below subchondral bone to access bone marrow to facilitate healing of bone defect 101. In the event that stent 12 extends from defect wall 16 after it has been positioned to access vascular zone 7, the remaining portion of stent 12 can be trimmed off (e.g., by a scalpel) to define a stent end terminating adjacent to tissue defect 16. In one exemplary embodiment, stent 12 is positioned such that one end thereof terminates adjacent to the tissue defect. In certain embodiments, positioning an end of stent 12 adjacent to a tissue defect means positioning an end of stent 12 a distance of not more than ¼ of the length of stent 12 from the tissue defect. In other embodiments, the end of stent 12 positioned adjacent a tissue defect will be positioned not more than 3 mm from the tissue defect. In certain embodiments, stent 12 will span a tissue defect in the meniscus and the meniscal rim.

FIG. 21 shows a perspective view of a stent 12 that is loaded onto a delivery needle 33 placed in contact with surface 40. In this position, the stent 12 is ready to be inserted into tissue. The stent indicated in this figure is the stent 12 of FIG. 17 except that it has the additional feature of a lead in chamfer 43 to facilitate ease of insertion initiation. Any of the stents 12 in the preceding figures could be shown in this figure, especially the stents 12 found in FIGS. 13, 14, 15, & 18;

A variety of materials may be used to manufacture stent 12. For example, stents could be manufactured from biocompatible polymers, biocompatible collagenous matrices, and/or any combination thereof. Other materials such as bioactive agents, biologically derived agents, inorganic materials that are biocompatible, cells, and biological lubricants can also be included as part of these components. Note that the term biocompatible polymers is intended to include both synthetic polymers and biologically derived polymers (i.e. collagen). Some examples of biocompatible polymers include: polyesters; poly-L-lactic acid (PLLA); polyglycolic acid (PGA); polydioxinone (PDS or PDO); polycaprilactone (PCL); polyvinyl alcohol (PVA); polyethylene oxide (PEO); poly(trimethylene carbonate); polymers disclosed in U.S. Pat. Nos. 6,333,029 and 6,355,699; polymers derived from tyrosine; polymers derived from chitosan; small intestine submucosa (SIS), urinary bladder submucosa, polymers derived from collagenous tissues; any other biocompatible polymer that is or is not bioabsorbable, or co-polymer, or mixture of polymers or co-polymers that are used in the construction of implants. In addition, as new biocompatible materials that may be or may not be bioabsorbable are developed, it is expected that at least some of them will be useful materials from which at least some of these components could be made. Also, the inner surface of stent 12 as well as the inner surface of the holes 27 could be configured such that an anti-coagulant material could be coated or chemically or otherwise bonded to the surface such that coagulation of the blood is impeded so as to facilitate blood flow. Note that the above materials are identified by way of example only, and the present invention is not limited to any particular material unless expressly called for in the claims.

A variety of materials may be used to manufacture the scaffold 20 of FIG. 12. For example, scaffold 20 could be manufactured from biocompatible polymers, biocompatible collagenous matrices, and/or any combination thereof. Other materials such as bioactive agents, biologically derived agents, inorganic materials that are biocompatible, cells, and biological lubricants can also be included as part of these components. Similar to the preceding paragraph the term biocompatible polymers is intended to include both synthetic polymers and biologically derived polymers (i.e. collagen), and the material listed above also apply to scaffold 20. The configuration of the scaffold material could be such that interconnective porosity is accomplished. This could via a variety of methods, including use of nonwoven or woven or knitted fibers, foam, sponge, etc. . . . material configurations. Again, note that the above materials are identified by way of example only, and the present invention is not limited to any particular material unless expressly called for in the claims. In one exemplary embodiment, stent 12 is at least as stiff as meniscal tissue.

When referring to ribs (36, 39), fins 38, or threads 37, the number of such could be one or more. Also, any combination of such features could be included in a stent 12.

The stents illustrated in FIGS. 13-18 and 24-25 are intended to be surgically implanted into tissue for use in helping with the repair of avascular 5 or limited vascular 6 tissue. FIG. 2 is a schematic of a human knee meniscus tissue that contains a range of vasculature. In the outer third of the periphery 3, the vasculature is abundant (red zone—7); whereas, the inner third of the meniscus has no vasculature (white zone—5), and the middle third of the meniscus has limited vasculature (red/white zone—6). When a tear or defect 11 occurs in the white 5 or red/white 6 zone as shown in FIG. 3, the probability of a successful repair occurring when standard repair techniques are employed is much lower than tears or defects 11 that occur in the red zone 7 because of the lack of blood or nutrients in the white 5 or red/white 6 zones. Therefore, a stent 12, if inserted through the outer tear surface wall 10 (FIG. 4) or through both the outer tear surface wall 10 and inner tear surface wall 9 as shown in FIG. 6 and continues through the meniscal tissue to or through the red zone 7, would provide a channel 28 through which blood, nutrients, and cells could travel to the tear surfaces 9, 10 and, thus, facilitate healing of the compromised tissue. Blood can enter into the stent 12 through the end 13 of stent 12 that is inserted in the red zone 7 and/or through the holes 27 (or porosity) in the stent 12 wall (25,26). If the stent outer surface 25 were configured and the stent 12 positioned such that it could adequately approximate the tear surfaces 9 & 10 as shown in FIG. 3 (i.e. external threads 37 either consistent or variable pitch or circumferential ribs 36 or fins 38, etc. . . . ) and secure those surfaces as illustrated in FIG. 6, the stent 12 could also function as a fixation device for the tear 11.

In addition to facilitating the healing of avascular or partially vascular meniscal tears, the stents illustrated in FIGS. 13-18 and 24-25 could also be implanted surgically to facilitate healing after a partial meniscectomy (FIG. 8) of the white 5 or red/white 6 zone is performed with or without an implant or regeneration scaffold 20 in place. After a partial meniscectomy is performed (FIG. 8), the stent 12 would be inserted through the outer defect wall 16 as illustrated in FIG. 10 and continue to or through the red zone 7 of the meniscus. After the stent 12 is positioned, the meniscal implant or regeneration device 20 could be implanted into the defect created by the partial meniscectomy with whatever surgical technique is appropriate as shown in FIG. 12. The stent 12 will then function to maintain a channel 28 to allow blood, nutrients, and cells to travel to the meniscal implant or regeneration device 20 such that regeneration is facilitated. Note that the stent 12 could also be used, not only to provide a channel 28 to the vascular 7 portion, but as a fixation device to attach the meniscal implant or regeneration device 20 to the outer defect wall 16 of the meniscus. Note also that the stent 12 could be used without the meniscal implant or regeneration device 20. In this case, the stent would provide a pathway for blood to find its way to the defect and eventually clot such that a blood clot would be delivered in situ to the defect site. The clot would then become the scaffold (or meniscal implant or regeneration device 20). Alternatively or in addition to, a substance could be injected through the stent 12 outer opening 13 that could then become the meniscal implant or regeneration device 20.

Figure 29:
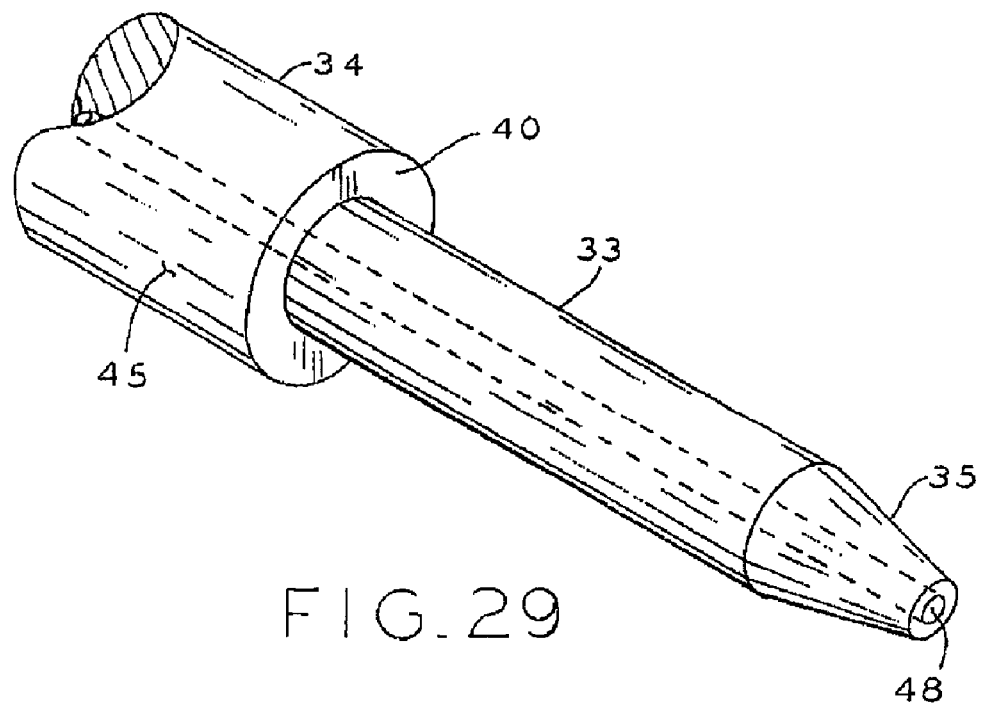
FIG. 29 shows a perspective view of a driver having a cannula.

Stents 12 illustrated in FIGS. 13-18 and 24-25 could be implanted surgically using the driver 45 of FIG. 20A. The stent 12 could be sized to fit over the smaller diameter shaft 33 of the driver as indicated in FIGS. 20B, 21, 22, 27 The larger diameter shaft 34 of the driver acts as a shoulder 40 to push the stent 12 into the tissue. The sharp tip 35 of the smaller diameter shaft 33 would pierce or cut the meniscal tissue to allow the stent 12 to be inserted into the hole 13 that is created in the meniscus (FIGS. 22 and 23). Upon retraction of the driver, the stent 12 would remain in the tissue, being held in the tissue by friction between the stent 12 and the tissue. This frictional resistance force could be increased, depending on the design of the ribs 36, fins 38, or roughness of the outer surface 25. The stent 12 would, thus, provide a channel 28 through which blood, nutrients, and cells could travel and reside. The driver (FIG. 20A) could have an axial actuation feature between the smaller diameter shaft 33 and the large diameter shaft 34 such that after the stent device 12 is inserted in the tissue, the smaller diameter shaft 33 is retracted while maintaining the position of the larger diameter shaft 34 against the stent device 12, thus, effectively preventing the stent device 12 from retracting during the removal of the smaller diameter shaft 33. Note that the driver of FIGS. 20A & 21, could also be cannulated (i.e. have a through hole 48 along its long axis as shown in FIG. 29) such that it can be inserted over a needle (i.e. guide needle). The guide needle could be inserted first using an "all inside" or "inside-out" arthroscopic surgical technique for instance, with Linvatec's (a Conmed co.) Zone Specific® cannulae or Sharpshooter® tissue repair system. These systems allow for delivery of flexible needles to specific areas of the meniscus or knee. After the guide needle is in position, the driver (with cannulation) and stent 12 of FIG. 21 could be fed over the guide needle and into the tissue until it is in position using an "all inside" or "outside-in" arthroscopic surgical technique. Also note that the above "all inside" or "outside-in" arthroscopic surgical technique for delivery of the stent 12 could be accomplished without the use of a guide needle. Note these arthroscopic surgical techniques are commonly used by orthopaedic surgeons throughout the world.

In addition to the aforementioned push in delivery technique that has just been described above, the threaded 36 stent 12 of FIGS. 16A or 16B could be delivered with driver 45 with a delivery needle 33 that matches the non-circular cross section 40 of the internal dimension of the stent 12. Using the identical "all inside" or "inside-out" arthroscopic surgical technique described above to delivery a guide needle and the "all inside" or "outside-in" arthroscopic surgical technique described above to deliver the stent 12. The only difference is that the threaded 36 stent 12 would be turned or screwed into position as opposed to pushed into position. Therefore, the threaded 36 stent 12 position could be more easily adjusted after initial fixation has occurred.

In addition to being used in the knee for blood, nutrient, and cells to travel to defects that occur in the avascular 7 or partially vascular 6 areas of the meniscus such that repair or regeneration can occur, the stent 12 described and illustrated in the figures could also be used in many other tissues throughout the body that have similar vascular/avascular anatomies. For instance, it could be used in the labrum of the hip joint, the labrum of the shoulder joint, the meniscal-like structure of the wrist, the discs of the spine, the disc of the temporomandibular joint, diseased cardiac muscle (i.e. due to reduced blood flow from cardiovascular blockage) to name a few.

It not only could be used in "soft tissue" such as meniscus, discs, labrum, cartilage, etc. . . . , but it could also be used in bone. For instance, in spinal applications when a patient presents to a surgeon with a bulging or herniated or ruptured spinal disc, the adjacent vertebral bone is often sclerotic (i.e. thickened or denser). Since much of the nutrients for the spinal disc are delivered via diffusion through the vertebral endplates, the sclerotic bone could tend to decrease the amount of nutrients delivered to the disc, thus contributing to the diseased state of the disc; therefore, if one or more stents 12 were placed through the sclerotic bone of the adjacent vertebra, then blood, nutrients, and cells could be delivered to the damaged or diseased disc and, thus, facilitate repair of the tissue. Also, for cartilage or cartilage/bone defects caused by the disease called osteochondritis dessicans (OCD), the typical surgical treatment is to remove the cartilage defect and then proceed to microfracture or microdrill the subchondral bone (i.e. the bone beneath the articular cartilage defect) to induce bleeding and provide a pathway for bone marrow components to aid in the healing of the OCD lesion. Therefore, the surgeon, in addition to or instead of microfracturing and microdrilling, could insert one or more stents 12 into the subchondral bone so that a channel would be retained in the bone such that blood, marrow components, nutrients, and cells could have access to the OCD lesion, thus, improving the healing capacity of that tissue site. Also, the stent 12 could be used in bone applications where non-union fractures occur. For instance, it could be inserted into the bone on either side of the fracture point(s) such that a fresh hematoma (mass of blood) may be created at or near the fracture site and thus facilitate repair or union of the fracture.

While most of the descriptions here have referred to a single stent 12 in these applications, it is likely that multiple stents 12 will be used to facilitate the repair of tissue. The spacing between stents 12 will depend on the tissue to be healed, the extent of damage, the type of defect, the native tissue, etc. . . . ; however, for a typical vertical tear that may occur in the knee meniscus avascular 7 or partially vascular 6 area, the spacing will likely be in the 5-10 mm range with larger or smaller spacing potentially.

After the stent 12 is implanted in tissue, it could also function as a portal through which biological treatments [i.e. blood, blood components, platelet rich plasma, tissue, bone marrow, bone marrow components, stem cells, fibroblast cells, synoviocyte cells, other cells, angiogenic factors (new blood vessel formation growth factors such as VEGF, IGF, etc. . . . ), other growth factors, hyaluronic acid, gene therapies, other biologic molecules etc.], drugs [analgesic, anti-clotting, clotting, anti-inflammatory, anti-infectives, etc. . . . ], and other substances could be delivered to area of interest. In addition to acting as a portal, stent 12 could also be coated with the biological treatments, drugs and other substances referred to in the preceding sentence. The treatment could enhance or initiate healing, increase blood flow, improve angiogenesis, induce or prevent clotting in the duct and tear/defect, deliver cells, deliver growth factors, deliver biologic elements, etc.

As used herein, passage of fluid refers to passage of blood, cells, growth factors, biological components, blood vessels, and the like. In regard to blood, passage or flow through stent 12 will occur for some time after which the blood will clot through a series of biological processes, thus forming a fibrin clot within the stent. The clot is rich in growth factors and biological material that has chemo-attractant capabilities and, thus, can send out biochemical signals to attract cells. Thus, the biochemical environment of the clot along with its physical structure allow for cells to infiltrate, travel through, and thrive within the stent as they proceed to the defect at the opposite end of the stent. As the cells travel through the stent via the clot, they lay down new tissue and new blood vessels such that healing can occur within the tissue and at or near the defect. Passage of cells through the clot is also encompassed by the phase "passage of fluid", as that phrase is used in this document.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for facilitating healing of a tissue defect residing in an area of tissue, comprising:
providing a stent including an elongate body having a first end, a second end, and a length, the elongate body configured to allow passage of fluid therethrough;
inserting the stent into the area of tissue; and
positioning the stent so that a vascular area of tissue is accessible by the stent and the second end of the stent terminates adjacent to the tissue defect, whereby biological material from the vascular area of tissue is capable of traveling through the stent to the tissue defect to facilitate healing the tissue defect.

2. The method of claim 1, wherein the step of inserting the stent into the area of tissue includes separating the tissue to provide an access for the stent without removing or ablating tissue.

3. The method of claim 1, wherein the tissue defect resides in an avascular or partially vascular area of tissue.

4. The method of claim 1, wherein the tissue defect is a tissue defect in a meniscus;
wherein the step of inserting the stent into the area of tissue includes inserting the stent into the meniscus.

5. The method of claim 1, wherein the tissue defect is a tissue defect in an area of cartilage of a bone;
wherein the step of inserting the stent into the area of tissue includes inserting the stent into the bone; and
wherein the step of positioning the stent so that a vascular area of tissue is accessible by the stent and the second end of the stent terminates adjacent to the tissue defect includes positioning the stent so that biological material of the bone is accessible by the stent and the second end of the stent terminates adjacent to the tissue defect.

6. The method of claim 1, further comprising:
delivering a biological treatment to the tissue defect via the stent.

7. The method of claim 6, wherein the step of delivering a biological treatment to the tissue defect via the stent includes:
placing the biological treatment in fluid communication with the stent, whereby the biological treatment is capable of traveling through the stent to the tissue defect.

8. The method of claim 6, wherein the step of delivering a biological treatment to the tissue defect via the stent includes:
coating the stent with the biological treatment.

9. The method of claim 6, wherein the biological treatment includes platelet rich plasma.

10. The method of claim 6, wherein the biological treatment includes bone marrow.

11. The method of claim 6, wherein the biological treatment includes stem cells.

12. The method of claim 6, wherein the biological treatment includes blood.

13. The method of claim 6, wherein the biological treatment includes growth factors.

14. The method of claim 1, wherein the positioning step includes trimming the stent to define the second end of the stent, whereby the second end defined by the trimming step terminates adjacent to the tissue defect.

15. The method of claim 1, wherein the stent further includes a hollow tube which is open at both the first and the second ends of the stent to define end apertures, the positioning step including positioning the end aperture residing at the second end of the stent adjacent to the tissue defect.

16. The method of claim 15, wherein the hollow tube includes a wall having a plurality of apertures sized to enable blood, nutrients and cells to enter the stent from the vascular area of tissue.

17. The method of claim 1, wherein the stent is a porous rod.

18. The method of claim 1, wherein an outer surface of the stent is smooth.

19. The method of claim 1, wherein an outer surface of the stent is roughened.

20. The method of claim 1, wherein an outer surface of the stent includes a rib.

21. The method of claim 1, wherein an outer surface of the stent includes a plurality of ribs that encircle the outer surface.

22. The method of claim 20, wherein the rib includes a thread, and wherein the positioning step includes threading the stent into the area of tissue.

23. The method of claim 22, wherein the thread has a consistent pitch.

24. The method of claim 1, wherein an outer surface of the stent includes a plurality of ribs that are substantially longitudinal and substantially parallel to a longitudinal axis of the stent.

25. The method of claim 1, wherein the stent includes a collar for limiting the travel of the stent into tissue.

26. The method of claim 1, wherein the positioning step positions the second end of the stent a distance of not more than one-quarter of the length of the stent from the tissue defect.

27. The method of claim 1, wherein the positioning step positions the second end of the stent a distance of not more than three millimeters from the tissue defect.

28. The method of claim 1, wherein the positioning step positions the stent so that the vascular area of tissue is accessible by the first end of the stent.

29. The method of claim 1, wherein the biological material is selected from the group consisting of blood, blood components, cells, tissue, growth factors, bone marrow, bone marrow components, and stem cells.

30. The method of claim 4, wherein the step of inserting the stent into the meniscus includes inserting the stent into the meniscus through the tissue defect.

31. A method for facilitating healing of a tissue defect residing in an area of tissue, comprising:
providing a stent including an elongate body having a first end and a second end, the elongate body configured to allow passage of fluid therethrough;
separating the tissue to allow insertion of the stent into the separated tissue without removing or ablating tissue;
inserting the stent into the separated tissue; and
positioning the stent so that a vascular area of tissue is accessible by the stent.

32. The method of claim 31, wherein the positioning step further includes:
positioning the stent so that the second end of the stent terminates adjacent to the tissue defect, whereby biological material from the vascular area of tissue is capable of traveling through the stent to the tissue defect to facilitate healing the tissue defect.

33. The method of claim 31, wherein the tissue defect resides in an avascular or partially vascular area of tissue.

34. The method of claim 31, wherein the tissue defect is a tissue defect in a meniscus;
wherein the step of inserting the stent into the separated tissue includes inserting the stent into the meniscus.

35. The method of claim 31, wherein the tissue defect is a tissue defect in an area of cartilage of a bone;
wherein the step of inserting the stent into the separated tissue includes inserting the stent into the bone;
wherein the step of positioning the stent so that a vascular area of tissue is accessible by the stent includes positioning the stent so that biological material of the bone is accessible by the stent and the second end of the stent terminates adjacent to the tissue defect.

36. The method of claim 31, further comprising:
delivering a biological treatment to the tissue defect through the stent.

37. The method of claim 36, wherein the step of delivering a biological treatment to the tissue defect through the stent includes:
placing the biological treatment in fluid communication with the stent, whereby the biological treatment is capable of traveling through the stent to the tissue defect.

38. The method of claim 36, wherein the step of delivering a biological treatment to the tissue defect through the stent includes:
coating the stent with the biological treatment.

39. The method of claim 36, wherein the biological treatment includes platelet rich plasma.

40. The method of claim 36, wherein the biological treatment includes bone marrow.

41. The method of claim 36, wherein the biological treatment includes stem cells.

42. The method of claim 36, wherein the biological treatment includes blood.

43. The method of claim 36, wherein the biological treatment includes growth factors.

44. The method of claim 31, wherein the positioning step includes trimming the stent to define the second end of the stent, whereby the second end defined by the trimming step terminates adjacent to the tissue defect.

45. The method of claim 31, wherein the stent further includes a hollow tube which is open at both the first and the second ends of the stent to define end apertures, the positioning step including positioning the end aperture residing at the second end of the stent adjacent to the tissue defect.

46. The method of claim 45, wherein the hollow tube includes a wall having a plurality of apertures sized to enable blood, nutrients and cells to enter the stent from the vascular area of tissue.

47. The method of claim 31, wherein the stent is a porous rod.

48. The method of claim 31, wherein an outer surface of the stent is smooth.

49. The method of claim 31, wherein an outer surface of the stent is roughened.

50. The method of claim 31, wherein an outer surface of the stent includes a rib.

51. The method of claim 31, wherein an outer surface of the stent includes a plurality of ribs that encircle the outer surface.

52. The method of claim 50, wherein the rib includes a thread, and wherein the positioning step includes threading the stent into the area of tissue.

53. The method of claim 52, wherein the thread has a consistent pitch.

54. The method of claim 31, wherein an, outer surface of the stent includes a plurality of ribs that are substantially longitudinal and substantially parallel to a longitudinal axis of the stent.

55. The method of claim 31, wherein the stent includes a collar for limiting the travel of the stent into tissue.

56. The method of claim 31, wherein the positioning step positions the second end of the stent a distance of not more than one-quarter of the length of the stent from the tissue defect.

57. The method of claim 31, wherein the positioning step positions the second end of the stent a distance of not more than three millimeters from the tissue defect.

58. The method of claim 31, wherein the positioning step positions the stent so that the vascular area of tissue is accessible by the first end of the stent.

59. The method of claim 34, wherein the step of inserting the stent into the meniscus includes inserting the stent into the meniscus through the tissue defect.

* * * * *